US007041876B2

(12) United States Patent
Beer et al.

(10) Patent No.: US 7,041,876 B2
(45) Date of Patent: May 9, 2006

(54) OOMYCETE-RESISTANT TRANSGENIC PLANTS BY VIRTUE OF PATHOGEN-INDUCED EXPRESSION OF A HETEROLOGOUS HYPERSENSITIVE RESPONSE ELICITOR

(75) Inventors: Steven V. Beer, Ithaca, NY (US); David W. Bauer, Kirkland, WA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 114 days.

(21) Appl. No.: 09/770,693

(22) Filed: Jan. 26, 2001

(65) Prior Publication Data

US 2002/0069434 A1 Jun. 6, 2002

Related U.S. Application Data

(60) Provisional application No. 60/178,565, filed on Jan. 26, 2000.

(51) Int. Cl.
*A01H 5/00* (2006.01)
*C12N 5/04* (2006.01)
*C12N 1/21* (2006.01)
*C12N 15/82* (2006.01)

(52) U.S. Cl. ................... 800/301; 800/317.3; 800/279; 800/288; 800/294; 800/293; 424/93.2; 435/320.1; 435/252.2; 435/418

(58) Field of Classification Search ................ 800/279, 800/288, 294, 293, 301, 317.3, 298; 435/418, 435/419, 430, 320.1, 252.3, 414; 536/23.7
See application file for complete search history.

(56) References Cited

U.S. PATENT DOCUMENTS 5,708,139 A 1/1998 Collmer et al.
5,723,760 A 3/1998 Strittmatter et al.
5,750,874 A 5/1998 Strittmatter et al.
5,776,889 A 7/1998 Wei et al.
5,849,868 A 12/1998 Beer et al.
5,850,015 A * 12/1998 Bauer et al. ................ 800/279
5,858,786 A 1/1999 Collmer et al.
5,859,324 A 1/1999 Wei et al.
5,859,332 A 1/1999 Strittmatter et al.
5,977,060 A * 11/1999 Zitter et al. .................... 514/2
5,981,843 A * 11/1999 Chappell et al. ............ 800/301
6,001,959 A 12/1999 Bauer et al.
6,172,184 B1 1/2001 Collmer et al.
6,174,717 B1 * 1/2001 Beer et al. ............. 435/252.33
6,228,644 B1 * 5/2001 Bogdanove et al. ........ 435/419
6,235,974 B1 5/2001 Qiu et al.
6,262,018 B1 7/2001 Kim et al.
6,277,814 B1 * 8/2001 Qiu et al. ...................... 514/2
6,342,654 B1 * 1/2002 Li et al. ..................... 800/279

FOREIGN PATENT DOCUMENTS

WO WO 98/32844 7/1998
WO WO 98/54214 12/1998
WO WO 99/11133 3/1999
WO WO 00/20452 4/2000
WO WO 00/20616 4/2000
WO WO 00/28055 * 5/2000
WO WO 01/98501 * 12/2001

OTHER PUBLICATIONS

Bonas, 1994, Trends Microbiol 2:1-2.*
Bonas, 1994, Curr. Topics Microbiol. Immunol. 192:79-98.*
Preston et al, 1995, Mol Plant Microbe Interact. 8:717-732.*
Addul-Kader et al, 1999, Acta Hort. 489:247-250.*
GenBank Accession No. U12639, 2000.*
Scorza et al, 1996, J. Amer. Hort. Sci. 121:616-619.*
Pfitzner et al, 1987, Nuc. Acids Res. 15:4449-4465.*
Gopalan et al, Plant Disease 80: 604-10 (1996).*
Bauer et al, MPMI 8441: 484-91 (1995).*
Cui et al, MPMI 947: 565-73 (1996).*
Ahmad et a1, 8th Int'l Cong. Molec. Plant Microbe Inter. Jul. 14-19, 1996.*
Bonas, Current Topics in Microbiologv and Immunology 192: 79-98 (1994).*
Alfano et al, Journal of Bacteriology 179: 5855-5662 (1997).*
Swanson et al, Phytopathology 90: s75 (1999).*
Bogdanove et a 1, Molec.Microbiol. 20:681-83 (1996).*
Wei et al, MPMI 13:1251-1262 (2000).*
van Dijk et al, J. Bacteriol. 181(16):4790-4797 (1999).*
Alfano et al, MPMI 10:580-588 (1997).*
Collmer et al Trends in Microbiol. 10:462-469 (2002).*
Belbahri et al, Plant J. 28:419-430 (2001).*
Kim et al, 1998, J. Bacteriol. 180:5203-5210.*
He et al, 1993, Cell 73:1255-1266.*
Buttner et al, 2002, EMBO J 21:5313-5322.*
Alfano et al, 1997, J. Bacteriol. 179:5655-5662.*
Ponchet et al, 1999, Cell. Mol. Life Sci. 56:1020-1047.*

(Continued)

*Primary Examiner*—Anne Kubelik
(74) *Attorney, Agent, or Firm*—Nixon Peabody LLP

(57) ABSTRACT

The present invention relates to a chimeric gene that includes a first DNA molecule encoding a hypersensitive response elicitor protein or polypeptide, a promoter operably linked 5' to the first DNA molecule to induce transcription of the first DNA molecule in response to activation of the promoter by an oomycete, and a 3' regulatory region operably linked to the first DNA molecule. Also disclosed are an expression system and a host cell containing the chimeric gene. The present invention also relates to a transgenic plant resistant to disease resulting from oomycete infection, the transgenic plant including the chimeric gene, wherein the promoter induces transcription of the first DNA molecule in response to infection of the plant by an oomycete. Transgenic seeds and transgenic cultivars obtained from the transgenic plant are also disclosed. Additional aspects of the present invention include methods of making a recombinant plant cell and a transgenic plant.

41 Claims, 6 Drawing Sheets

OTHER PUBLICATIONS

Bauer et al, 1999, Acta Hort. 489:301-304.*

Doerner et al, 1990, Bio/Technol. 8:845-848.*

Kawamata et al, 1997, Plant Cell Physiol. 38:792-803.*

Gopalan et al, 1996, Plant Cell, 8:1095-1105.*

Keller et al., "Pathogen-Induced Elicitin Production in Transgenic Tobacco Generates a Hypersensitive Response and Nonspecific Disease Resistance," *The Plant Cell* 11: 223-235 (1999).

Rugang et al., "Reduction of Lesion Growth Rate of Late Blight Plant Disease in Transgenic Potato Expressing Harpin Protein," *Science in China* 42(1):96-101 (1999).

Hart et al., "Regulated Inactivation of Homologous Gene Expression in Transgenic *Nicotiana sylvestris* Plants Containing a Defense-Related Tobacco Chitinase Gene," *Mol. Gen. Genet*. 235:179-188 (1992).

Wei et al., "Harpin, Elicitor of the Hypersensitive Response Produced by the Plant Pathogen *Erwinia amylovora*," *Science* 257:85-88 (1992).

Bauer et al., "New Transgenic Approaches for Possible Increased Resistance to Fire Blight," 8th International Workshop on Fire Blight, International Society for Horticultural Science, Kusadasi, Turkey (Oct. 12-15, 1998) (Abstract).

* cited by examiner

OOMYCETE-RESISTANT TRANSGENIC PLANTS BY VIRTUE OF PATHOGEN-INDUCED EXPRESSION OF A HETEROLOGOUS HYPERSENSITIVE RESPONSE ELICITOR

This application claims the benefit of U.S. Provisional Patent Application Ser. No. 60/178,565, filed Jan. 26, 2000, which is hereby incorporated by reference in its entirety.

This invention was made in part with support by the U.S. Government under Grant No. 97-34367-3937 from the U.S. Department of Agriculture. The U.S. Government may have certain rights in this invention.

FIELD OF THE INVENTION

The present invention relates to transgenic plants resistant to oomycete infection which contain a heterologous hypersensitive response elicitor under the control of a promoter responsive to infection by an oomycete.

BACKGROUND OF THE INVENTION

In general, fungal plant diseases can be classified into two types: those caused by soilborne fungi and those caused by airborne fungi. Soilborne fungi cause some of the most widespread and serious plant diseases, such as root and stem rot caused by *Fusarium* spp. and root rot caused by *Phytophthora* spp. For example, *Phytophthora parasitica* var. *nicotiana*, a soilborne oomycete found in many tobacco growing regions worldwide, causes black shank, a highly destructive root and stem rot disease of many varieties of cultivated tobacco.

Since airborne fungi can be spread long distances by wind, they can cause devastating losses, particularly in crops which are grown over large regions. A number of pathogens have caused widespread epidemics in a variety of crops. Important diseases caused by airborne fungi are stem rust (*Puccinia graminis*) on wheat, corn smut (*Ustilago maydis*) on corn, and late blight disease (*Phytophthora infestans*) on potato and tomato. *Plasmopera viticola* is an airborne oomycete that causes downy mildew disease on grape vines. The blue mold fungus (*Peronospora tabacina*) has caused catastrophic losses in tobacco crops, particularly in the United States and Cuba.

Most of these fungal diseases are difficult to combat, and farmers and growers must use a combination of practices, such as sanitary measures, resistant cultivars, and effective fungicide against such diseases. Hundreds of millions of dollars are spent annually for chemical control of plant-pathogenic fungi. As a result, there is today a real need for new, more effective and safe means to control plant-pathogenic fungi, particularly oomycetes which are responsible for major crop loss.

Genetic engineering promises to be an effective strategy for reducing the losses associated with diseases of field crops. Several successful approaches have been reported where the constitutive expression of antimicrobial peptides such as cecropins (Arce et al., "Enhanced Resistance to Bacterial Infection by Erwinia Carotovora Susp. Atroseptica in Transgenic Potato Plants Expressing the Attacin or the Cecropin SB-37 Genes," *Am. J. Potato Res.* 76:169–177 (1999)), lysozyme (Nakajima et al., "Fungal and Bacterial Disease Resistance in Transgenic Plants Expressing Human Lysozyme," *Plant Cell Reports* 16:674–679 (1997)), and monoclonal antibodies (Tavladoraki et al, "Transgenic Plants Expressing a Functional Single Chain FV Antibody are Specifically Protected from Virus Attack," *Nature* 366: 468–472 (1993)) effectively protected plants from parasitic organisms. However successful, these approaches have limited application to food production since many of these antimicrobial peptides and plant defense molecules are potentially toxic or allergenic to humans (Franck-Oberaspach et al., "Consequences of Classical and Biotechnological Resistance Breeding for Food Toxicology and Allergenicity," *Plant Breeding* 116:1–17 (1997)). Thus, alternative approaches for genetically engineering disease resistance would be more desirable.

Plants posses a highly evolved pathogen surveillance system which allows for recognition of specific pathogen derived molecules known as elicitors. Elicitor recognition results in an incompatible plant-microbe interaction, defined as the rapid activation of plant defense genes, typically resulting in the hypersensitive response and the onset of systemic acquired resistance.

The hypersensitive response is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise*, Vol. 5, J. G. Horsfall and E. B. Cowling, ed. Academic Press New York (1980); Klement, Z., "Hypersensitivity," pages 149–177 in: *Phytopathogenic Prokaryotes*, Vol. 2, M. S. Mount and G. H. Lacy, ed. Academic Press, New York (1982)). The hypersensitive response elicited by bacteria is readily observed as a tissue collapse if high concentrations ($\geqq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199: 299–300; Klement, et al., "Hypersensitive Reaction Induced by Phytopathogenic Bacteria in the Tobacco Leaf," *Phytopathology* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in *Phytopathogenic Prokarvotes*, Vol. 2., M. S. Mount and G. H. Lacy, ed. Academic Press, New York (1982)). The capacities to elicit the hypersensitive response in a nonhost and be pathogenic in a host appear linked. As noted by Klement, Z., "Hypersensitivity," pages 149–177 in *Phytopathogenic Prokaryotes*, Vol. 2., M. S. Mount and G. H. Lacy, ed. Academic Press, New York, (1982), these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991)). Consequently, the hypersensitive response may hold clues to both the nature of plant defense and the basis for bacterial pathogenicity.

The hrp genes are widespread in Gram-negative plant pathogens, where they are clustered, conserved, and in some cases interchangeable (Willis, D. K., et al., "hrp Genes of Phytopathogenic Bacteria," *Mol. Plant-Microbe Interact.* 4:132–138 (1991); Bonas, U., "hrp Genes of Phytopathogenic Bacteria," pages 79–98 in: *Current Topics in Microbiology and Immunology: Bacterial Pathogenesis of Plants and Animals—Molecular and Cellular Mechanisms*, J. L.

Dangl, ed. Springer-Verlag, Berlin (1994)). Several hrp genes encode components of a protein secretion pathway similar to one used by Yersinia, Shigella, and *Salmonella* spp. to secrete proteins essential in animal diseases (Van Gijsegem, et al., "Evolutionary Conservation of Pathogenicity Determinants Among Plant and Animal Pathogenic Bacteria," *Trends Microbiol.* 1:175–180 (1993)). In *E. amylovora, P. syringae*, and *P. solanacearum*, hrp genes have been shown to control the production and secretion of glycine-rich, protein elicitors of the hypersensitive response (He, S. Y., et al. "Pseudomonas Syringae pv. Syringae $Harpin_{PSS}$: a Protein that is Secreted via the Hrp Pathway and Elicits the Hypersensitive Response in Plants," *Cell* 73:1255–1266 (1993); Wei, Z. -M., et al., "HrpI of *Erwinia amylovora* Functions in Secretion of Harpin and is a Member of a New Protein Family," *J. Bacteriol.* 175:7958–7967 (1993); Arlat, M., et al. "PopA1, a Protein Which Induces a Hypersensitive-like Response on Specific Petunia Genotypes, is Secreted via the Hrp Pathway of Pseudomonas solanacearum," *EMBO J.* 13:543–553 (1994)).

The first of these proteins was discovered in *E. amylovora* Ea321, a bacterium that causes fire blight of rosaceous plants, and was designated harpin (Wei, Z. -M., et al, "Harpin, Elicitor of the Hypersensitive Response Produced by the Plant Pathogen *Erwinia amylovora," Science* 257: 85–88 (1992)). Mutations in the encoding hrpN gene revealed that harpin is required for *E. amylovora* to elicit a hypersensitive response in nonhost tobacco leaves and incite disease symptoms in highly susceptible pear fruit. The *P. solanacearum* GMI 1000 PopA 1 protein has similar physical properties and also elicits the hypersensitive response in leaves of tobacco, which is not a host of that strain (Arlat, et al., "PopA1, a Protein Which Induces a Hypersensitive-like Response on Specific Petunia Genotypes, is Secreted via the Hrp Pathway of Pseudomonas solanacearum," *EMBO J.* 13:543–53 (1994)). However, *P. solanacearum* popA mutants still elicit the hypersensitive response in tobacco and incite disease in tomato. Thus, the role of these glycine-rich hypersensitive response elicitors can vary widely among Gram-negative plant pathogens.

Other plant pathogenic hypersensitive response elicitors have been isolated, cloned, and sequenced. These include: *Erwinia chrysanthemi* (Bauer, et. al., "*Erwinia chrysanthemi* $Harpin_{Ech}$: Soft-Rot Pathogenesis," *MPMI* 8(4): 484–91 (1995)); *Erwinia carotovora* (Cui, et. al., "The $RsmA^-$ Mutants of *Erwinia carotovora* subsp. *carotovora* Strain Ecc71 Overexpress $hrpN_{Ecc}$, and Elicit a Hypersensitive Reaction-like Response in Tobacco Leaves," *MPMI* 9(7): 565–73 (1966)); *Erwinia stewartii* (Ahmad, et. al., "Harpin is not Necessary for the Pathogenicity of *Erwinia stewartii* on Maize," *8th Int'l. Cong. Molec. Plant-Microb. Inter.* Jul. 14–19, 1996 and Ahmad, et. al., "Harpin is not Necessary for the Pathogenicity of *Erwinia stewartii* on Maize," *Ann. Mtg. Am. Phytopath. Soc.* Jul. 27–31, 1996); and *Pseudomonas syringae pv. syringae* (WO 94/26782 to Cornell Research Foundation, Inc.).

Because the hypersensitive response results in localized necrosis of plant tissue, it is desirable to limit expression of a heterologous hypersensitive response elicitor to certain tissues in transgenic plants. This approach is discussed generally in PCT publication WO 94/01546 to Beer et al., but no specific transgenic plants are identified and only two suitable fungus-responsive promoters are suggested, e.g., the phenylalanine ammonia lyase and chalcone synthase promoters. No promoters responsive specifically to infection by oomycetes are identified therein.

The present invention is directed to overcoming these and other deficiencies in the art.

SUMMARY OF THE INVENTION

The present invention relates to a chimeric gene that includes a first DNA molecule encoding a hypersensitive response elicitor protein or polypeptide, a promoter operably linked 5' to the first DNA molecule to induce transcription of the first DNA molecule in response to activation of the promoter by an oomycete, and a 3' regulatory region operably linked to the first DNA molecule. Also disclosed are an expression system that includes a vector in which is inserted a chimeric gene of the present invention and a host cell that includes a chimeric gene of the present invention.

Another aspect of the present invention relates to a transgenic plant resistant to disease resulting from oomycete infection. The transgenic plant includes a chimeric gene of the present invention, wherein the promoter induces transcription of the first DNA molecule in response to infection of the plant by an oomycete. Transgenic seeds and transgenic cultivars obtained from the transgenic plant are also disclosed.

An additional aspect of the present invention relates to a method of making a recombinant plant cell. This is accomplished by transforming a plant cell with a chimeric gene of the present invention under conditions effective to yield transcription of the first DNA molecule in response to oomycete-induced activation of the promoter.

A further aspect of the present invention relates to a method of making a plant resistant to disease resulting from oomycete infection. This is accomplished by transforming a plant cell with a chimeric gene of the present invention under conditions effective to yield transcription of the first DNA molecule in response to oomycete-induced activation of the promoter and regenerating the plant from the transformed plant cell.

The present invention confers oomycete-induced disease resistance to plants transformed with a chimeric gene encoding a hypersensitive response elicitor protein or polypeptide, which is transcribed within a limited population of plant cells in response to infection of the plant by an oomycete. To limit transcription of the chimeric gene within a certain population of plant cells, the chimeric gene includes a promoter that is responsive to infection by an oomycete (i.e., it is activated by the oomycete). The hypersensitive response elicitor protein or polypeptide can cause tissue collapse at the site of infection and/or induce systemic resistance against the oomycete and other pathogens. By using the promoter from the potato gst1 gene, for example, which is activated by infection with oomyceteous fungi, the present invention can control fungal pathogens within crops without harming the transgenic plant and without resorting to use of environmentally damaging chemicals.

BRIEF DESCRIPTION OF THE DRAWINGS

FIG. 3A is a Northern blot analysis performed using hrpN DNA as a probe. FIG. 3B is an ethidium bromide stained gel shown as a control (bottom).

FIG. 4A shows the effects of *P. parasitica* infection in WT *Arabidopsis* (control, left) and GSSN 8–4 *Arabidopsis* (test, right). FIG. 4B shows the degree of trypan blue staining of *P. parasitica*-infected leaves of WT (control, left) and GSSN 8–4 plants (test, right), both taken 10 days post-inoculation.

DETAILED DESCRIPTION OF THE INVENTION

Figure 1:
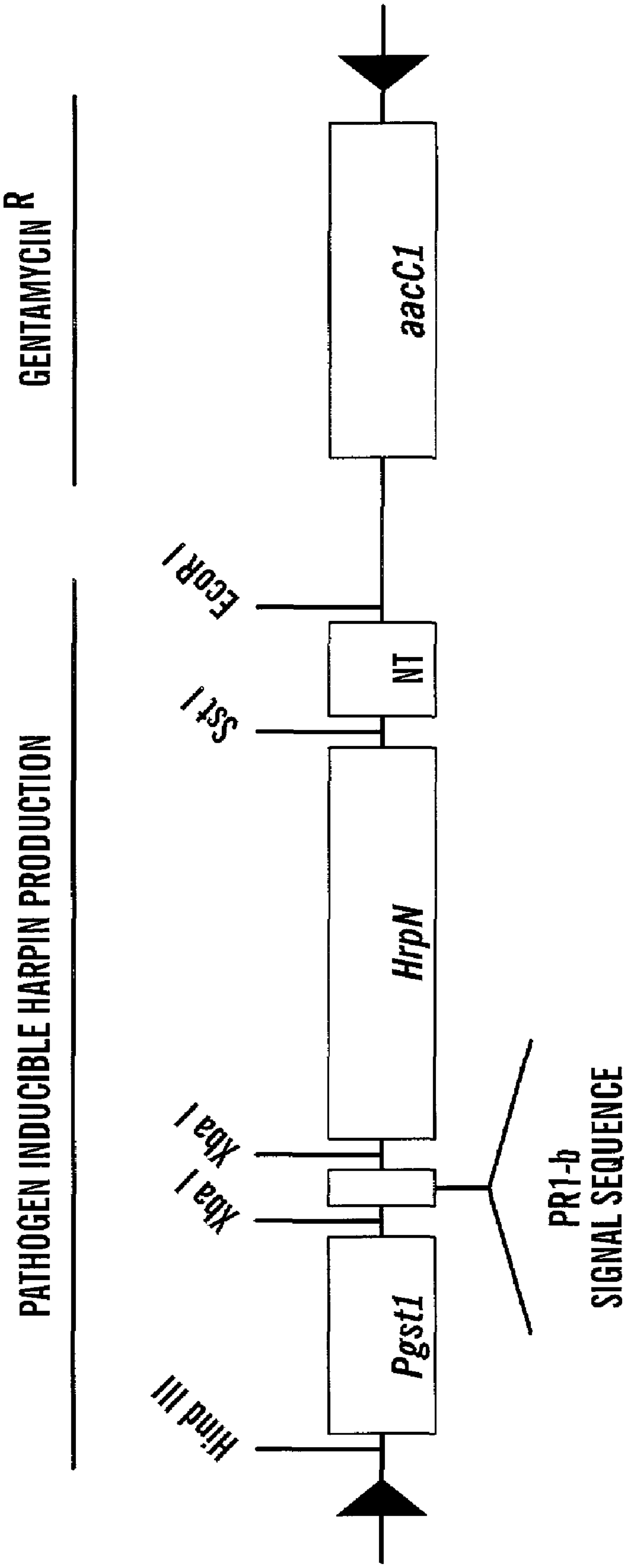
FIG. 1 is a schematic representation and partial restriction map of T-DNA in plant transformation vector pCPP1294. Filled triangles represent the left and right borders; Pgst1 represents the gst1 promoter from potato variety Atlantic; PR1-b represents the DNA molecule encoding a signal sequence from *Nicotiana tabacum*; hrpN represents the DNA molecule encoding the hypersensitive response elicitor $harpin_{Ea}$ of *Erwinia amylovora*; NT represents the nos terminating region; aacC1 represents the gentamycin resistance cassette.

One aspect of the present invention relates to a novel DNA construct in the form of a chimeric gene. The chimeric gene includes a first DNA molecule encoding a hypersensitive response elicitor protein or polypeptide, a promoter operably linked 5' to the first DNA molecule to induce transcription of the first DNA molecule in response to activation of the promoter by an oomycete, and a 3' regulatory region operably linked to the first DNA molecule. As discussed more fully hereinafter, a chimeric gene of the present invention is particularly useful in preparing a transgenic plant for the purpose of rendering the transgenic plant resistant to disease resulting from infection thereof by an oomycete.

The first DNA molecule can encode any hypersensitive response elicitor protein or polypeptide which is effective in triggering a hypersensitive response (i.e., in a particular host plant selected for transformation). Generally, it is desirable to express hypersensitive response elicitors only in plants which are non-hosts for the source organism of the hypersensitive response elicitor. Suitable hypersensitive elicitor proteins or polypeptides are those derived from a wide variety of bacterial and fungal pathogens, preferably bacterial pathogens.

Exemplary hypersensitive response elicitor proteins and polypeptides from bacterial sources include, without limitation, the hypersensitive response elicitors from*Erwinia* species (e.g., *Erwinia amylovora, Erwinia chrysanthemi, Erwinia stewartii, Erwinia carotovora*, etc.), *Pseudomonas* species (e.g., *Pseudomonas syringae, Pseudomonas solanacearum*, etc.), and *Xanthomonas* species (e.g., *Xanthomonas campestris*). In addition to hypersensitive response elicitors from these Gram-negative bacteria, it is possible to use elicitors from Gram-positive bacteria. One example is the hypersensitive response elicitor from *Clavibacter michiganensis* subsp. *sepedonicus.*

Exemplary hypersensitive response elicitor proteins or polypeptides from fungal sources include, without limitation, the hypersensitive response elicitors (i.e., elicitins) from various *Phytophora* species (e.g., *Phytophthora parasitica, Phytophthora cryptogea, Phytophthora cinnamomi, Phytophthora capsici, Phytophthora megasperma, Phytophthora citrophthora*, etc.).

Preferably, the first DNA molecule encodes a hypersensitive response elicitor protein or polypeptide of *Erwinia chrysanthemi, Erwinia amylovora, Pseudomonas syringae*, or *Pseudomonas solanacearum.*

The hypersensitive response elicitor protein or polypeptide from Erwinia chrysanthemi has an amino acid sequence corresponding to SEQ. ID. No. 1 as follows:

```
Met Gln Ile Thr Ile Lys Ala His Ile Gly Gly Asp Leu Gly Val Ser
1               5                   10                  15
Gly Leu Gly Ala Gln Gly Leu Lys Gly Leu Asn Ser Ala Ala Ser Ser
            20                  25                  30
Leu Gly Ser Ser Val Asp Lys Leu Ser Ser Thr Ile Asp Lys Leu Thr
        35                  40                  45
Ser Ala Leu Thr Ser Met Met Phe Gly Gly Ala Leu Ala Gln Gly Leu
    50                  55                  60
Gly Ala Ser Ser Lys Gly Leu Gly Met Ser Asn Gln Leu Gly Gln Ser
65                  70                  75                  80
Phe Gly Asn Gly Ala Gln Gly Ala Ser Asn Leu Leu Ser Val Pro Lys
                85                  90                  95
Ser Gly Gly Asp Ala Leu Ser Lys Met Phe Asp Lys Ala Leu Asp Asp
            100                 105                 110
Leu Leu Gly His Asp Thr Val Thr Lys Leu Thr Asn Gln Ser Asn Gln
        115                 120                 125
Leu Ala Asn Ser Met Leu Asn Ala Ser Gln Met Thr Gln Gly Asn Met
    130                 135                 140
Asn Ala Phe Gly Ser Gly Val Asn Asn Ala Leu Ser Ser Ile Leu Gly
145                 150                 155                 160
Asn Gly Leu Gly Gln Ser Met Ser Gly Phe Ser Gln Pro Ser Leu Gly
                165                 170                 175
```

-continued

```
Ala Gly Gly Leu Gln Gly Leu Ser Gly Ala Gly Ala Phe Asn Gln Leu
                180                 185                 190
Gly Asn Ala Ile Gly Met Gly Val Gly Gln Asn Ala Ala Leu Ser Ala
        195                 200                 205
Leu Ser Asn Val Ser Thr His Val Asp Gly Asn Asn Arg His Phe Val
    210                 215                 220
Asp Lys Glu Asp Arg Gly Met Ala Lys Glu Ile Gly Gln Phe Met Asp
225                 230                 235                 240
Gln Tyr Pro Glu Ile Phe Gly Lys Pro Glu Tyr Gln Lys Asp Gly Trp
                245                 250                 255
Ser Ser Pro Lys Thr Asp Asp Lys Ser Trp Ala Lys Ala Leu Ser Lys
            260                 265                 270
Pro Asp Asp Asp Gly Met Thr Gly Ala Ser Met Asp Lys Phe Arg Gln
        275                 280                 285
Ala Met Gly Met Ile Lys Ser Ala Val Ala Giy Asp Thr Gly Asn Thr
    290                 295                 300
Asn Leu Asn Leu Arg Gly Ala Gly Gly Ala Ser Leu Gly Ile Asp Ala
305                 310                 315                 320
Ala Val Val Gly Asp Lys Ile Ala Asn Met Ser Leu Gly Lys Leu Ala
                325                 330                 335
Asn Ala
```

This hypersensitive response elicitor protein or polypeptide has a molecular weight of 34 kDa, is heat stable, has a glycine content of greater than 16%, and contains substantially no cysteine. This *Erwinia chrysanthemi* hypersensitive response elicitor protein or polypeptide is encoded by a DNA molecule having a nucleotide sequence corresponding to SEQ. ID. No. 2 as follows:

```
cgattttacc cgggtgaacg tgctatgacc gacagcatca cggtattcga caccgttacg      460

gcgtttatgg ccgcgatgaa ccggcatcag gcggcgcgct ggtcgccgca atccggcgtc      120

gatctggtat ttcagtttgg ggacaccggg cgtgaactca tgatgcagat tcagccgggg      180

cagcaatatc ccggcatgtt gcgcacgctg ctcgctcgtc gttatcagca ggcggcagag      240

tgcgatggct gccatctgtg cctgaacggc agcgatgtat tgatcctctg gtggccgctg      300

ccgtcggatc ccggcagtta tccgcaggtg atcgaacgtt tgtttgaact ggcgggaatg      360

acgttgccgt cgctatccat agcaccgacg gcgcgtccgc agacagggaa cggacgcgcc      420

cgatcattaa gataaaggcg gctttttttta ttgcaaaacg gtaacggtga ggaaccgttt      480

caccgtcggc gtcactcagt aacaagtatc catcatgatg cctacatcgg gatcggcgtg      540

ggcatccgtt gcagatactt ttgcgaacac ctgacatgaa tgaggaaacg aaattatgca      600

aattacgatc aaagcgcaca tcggcggtga tttgggcgtc tccggtctgg ggctgggtgc      660

tcagggactg aaaggactga attccgcggc ttcatcgctg ggttccagcg tggataaact      720

gagcagcacc atcgataagt tgacctccgc gctgacttcg atgatgtttg gcggcgcgct      780

ggcgcagggg ctgggcgcca gctcgaaggg gctggggatg agcaatcaac tgggccagtc      840

tttcggcaat ggcgcgcagg gtgcgagcaa cctgctatcc gtaccgaaat ccggcggcga      900

tgcgttgtca aaaatgtttg ataaagcgct ggacgatctg ctgggtcatg acaccgtgac      960

caagctgact aaccagagca accaactggc taattcaatg ctgaacgcca gccagatgac     1020

ccagggtaat atgaatgcgt tcggcagcgg tgtgaacaac gcactgtcgt ccattctcgg     1080

caacggtctc ggccagtcga tgagtggctt ctctcagcct tctctggggg caggcggctt     1140

gcagggcctg agcggcgcgg gtgcattcaa ccagttgggt aatgccatcg gcatgggcgt     1200

ggggcagaat gctgcgctga gtgcgttgag taacgtcagc acccacgtag acggtaacaa     1260

ccgccacttt gtagataaag aagatcgcgg catggcgaaa gagatcggcc agtttatgga     1320

tcagtatccg gaaatattcg gtaaaccgga ataccagaaa gatggctgga gttcgccgaa     1380
```

-continued

```
gacggacgac aaatcctggg ctaaagcgct gagtaaaccg gatgatgacg gtatgaccgg      1440

cgccagcatg gacaaattcc gtcaggcgat gggtatgatc aaaagcgcgg tggcgggtga      1500

taccggcaat accaacctga acctgcgtgg cgcgggcggt gcatcgctgg gtatcgatgc      1560

ggctgtcgtc ggcgataaaa tagccaacat gtcgctgggt aagctggcca acgcctgata      1620

atctgtgctg gcctgataaa gcggaaacga aaaaagagac ggggaagcct gtctcttttc      1680

ttattatgcg gtttatgcgg ttacctggac cggttaatca tcgtcatcga tctggtacaa      1740

acgcacattt tcccgttcat tcgcgtcgtt acgcgccaca atcgcgatgg catcttcctc      1800

gtcgctcaga ttgcgcggct gatggggaac gccgggtgga atatagagaa actcgccggc      1860

cagatggaga cacgtctgcg ataaatctgt gccgtaacgt gtttctatcc gcccctttag      1920

cagatagatt gcggtttcgt aatcaacatg gtaatgcggt tccgcctgtg cgccggccgg      1980

gatcaccaca atattcatag aaagctgtct tgcacctacc gtatcgcggg agataccgac      2040

aaaatagggc agtttttgcg tggtatccgt ggggtgttcc ggcctgacaa tcttgagttg      2100

gttcgtcatc atctttctcc atctgggcga cctgatcggt t                          2141
```

The hypersensitive response elicitor protein or polypeptide derived from *Erwinia amylovora* has an amino acid sequence corresponding to SEQ. ID. No. 3 as follows:

```
Met Ser Leu Asn Thr Ser Gly Leu Gly Ala Ser Thr Met Gln Ile Ser
1               5                   10                  15
Ile Gly Gly Ala Gly Gly Asn Asn Gly Leu Leu Gly Thr Ser Arg Gln
            20                  25                  30
Asn Ala Gly Leu Gly Gly Asn Ser Ala Leu Gly Leu Gly Gly Gly Asn
        35                  40                  45
Gln Asn Asp Thr Val Asn Gln Leu Ala Gly Leu Leu Thr Gly Met Met
    50                  55                  60
Met Met Met Ser Met Met Gly Gly Gly Gly Leu Met Gly Gly Gly Leu
65                  70                  75                  80
Gly Gly Gly Leu Gly Asn Gly Leu Gly Gly Ser Gly Gly Leu Gly Glu
                85                  90                  95
Gly Leu Ser Asn Ala Leu Asn Asp Met Leu Gly Gly Ser Leu Asn Thr
            100                 105                 110
Leu Gly Ser Lys Gly Gly Asn Asn Thr Thr Ser Thr Thr Asn Ser Pro
        115                 120                 125
Leu Asp Gln Ala Leu Gly Ile Asn Ser Thr Ser Gln Asn Asp Asp Ser
    130                 135                 140
Thr Ser Gly Thr Asp Ser Thr Ser Asp Ser Ser Asp Pro Met Gln Gln
145                 150                 155                 160
Leu Leu Lys Met Phe Ser Glu Ile Met Gln Ser Leu Phe Gly Asp Gly
                165                 170                 175
Gln Asp Gly Thr Gln Gly Ser Ser Ser Gly Gly Lys Gln Pro Thr Glu
            180                 185                 190
Gly Glu Gln Asn Ala Tyr Lys Lys Gly Val Thr Asp Ala Leu Ser Gly
        195                 200                 205
Leu Met Gly Asn Gly Leu Ser Gln Leu Leu Gly Asn Gly Gly Leu Gly
    210                 215                 220
Gly Gly Gln Gly Gly Asn Ala Gly Thr Gly Leu Asp Gly Ser Ser Leu
225                 230                 235                 240
Gly Gly Lys Gly Leu Gln Asn Leu Ser Gly Pro Val Asp Tyr Gln Gln
                245                 250                 255
Leu Gly Asn Ala Val Gly Thr Gly Ile Gly Met Lys Ala Gly Ile Gln
            260                 265                 270
Ala Leu Asn Asp Ile Gly Thr His Arg His Ser Ser Thr Arg Ser Phe
        275                 280                 285
Val Asn Lys Gly Asp Arg Ala Met Ala Lys Glu Ile Gly Gln Phe Met
    290                 295                 300
Asp Gln Tyr Pro Glu Val Phe Gly Lys Pro Gln Tyr Gln Lys Gly Pro
305                 310                 315                 320
Gly Gln Glu Val Lys Thr Asp Asp Lys Ser Trp Ala Lys Ala Leu Ser
                325                 330                 335
Lys Pro Asp Asp Asp Gly Met Thr Pro Ala Ser Met Glu Gln Phe Asn
            340                 345                 350
```

-continued

```
Lys Ala Lys Gly Met Ile Lys Arg Pro Met Ala Gly Asp Thr Gly Asn
        355                 360                 365
Gly Asn Leu Gln Ala Arg Gly Ala Gly Gly Ser Ser Leu Gly Ile Asp
    370                 375                 380
Ala Met Met Ala Gly Asp Ala Ile Asn Asn Met Ala Leu Gly Lys Leu
385                 390                 395                 400
Gly Ala Ala
```

This hypersensitive response elicitor protein or polypeptide has a molecular weight of about 39 kDa, has a pI of approximately 4.3, and is heat stable at 100° C. for at least 10 minutes. This hypersensitive response elicitor protein or polypeptide has substantially no cysteine. The hypersensitive response elicitor protein or polypeptide derived from *Erwinia amylovora* is more fully described in Wei, Z-M., et al., "Harpin, Elicitor of the Hypersensitive Response Produced by the Plant Pathogen *Erwinia amylovora,*" *Science* 257:85–88 (1992), which is hereby incorporated by reference. The DNA molecule encoding this hypersensitive response elicitor protein or polypeptide has a nucleotide sequence corresponding to SEQ. ID. No. 4 as follows:

```
aagcttcggc atggcacgtt tgaccgttgg gtcggcaggg tacgtttgaa ttattcataa      60

gaggaatacg ttatgagtct gaatacaagt gggctgggag cgtcaacgat gcaaatttct     120

atcggcggtg cgggcggaaa taacgggttg ctgggtacca gtcgccagaa tgctgggttg     180

ggtggcaatt ctgcactggg gctgggcggc ggtaatcaaa atgataccgt caatcagctg     240

gctggcttac tcaccggcat gatgatgatg atgagcatga tgggcggtgg tgggctgatg     300

ggcggtggct taggcggtgg cttaggtaat ggcttgggtg gctcaggtgg cctgggcgaa     360

ggactgtcga acgcgctgaa cgatatgtta ggcggttcgc tgaacacgct gggctcgaaa     420

ggcggcaaca ataccacttc aacaacaaat tccccgctgg accaggcgct gggtattaac     480

tcaacgtccc aaaacgacga ttccacctcc ggcacagatt ccacctcaga ctccagcgac     540

ccgatgcagc agctgctgaa gatgttcagc gagataatgc aaagcctgtt tggtgatggg     600

caagatggca cccagggcag ttcctctggg ggcaagcagc cgaccgaagg cgagcagaac     660

gcctataaaa aaggagtcac tgatgcgctg tcgggcctga tgggtaatgg tctgagccag     720

ctccttggca acgggggact gggaggtggt cagggcggta atgctggcac gggtcttgac     780

ggttcgtcgc tgggcggcaa agggctgcaa aacctgagcg ggccggtgga ctaccagcag     840

ttaggtaacg ccgtgggtac cggtatcggt atgaaagcgg gcattcaggc gctgaatgat     900

atcggtacgc acaggcacag ttcaacccgt tctttcgtca ataaaggcga tcgggcgatg     960

gcgaaggaaa tcggtcagtt catggaccag tatcctgagg tgtttggcaa gccgcagtac    1020

cagaaaggcc cgggtcagga ggtgaaaacc gatgacaaat catgggcaaa agcactgagc    1080

aagccagatg acgacggaat gacaccagcc agtatggagc agttcaacaa agccaagggc    1140

atgatcaaaa ggcccatggc gggtgatacc ggcaacggca acctgcaggc acgcggtgcc    1200

ggtggttctt cgctgggtat tgatgccatg atggccggtg atgccattaa caatatggca    1260

cttggcaagc tgggcgcggc ttaagctt                                       1288
```

The hypersensitive response elicitor protein or polypeptide derived from *Pseudomonas syringae* has an amino acid sequence corresponding to SEQ. ID. No. 5 as follows:

```
Met Gln Ser Leu Ser Leu Asn Ser Ser Ser Leu Gln Thr Pro Ala Met
1               5                   10                  15
Ala Leu Val Leu Val Arg Pro Glu Ala Glu Thr Thr Gly Ser Thr Ser
            20                  25                  30
Ser Lys Ala Leu Gln Glu Val Val Val Lys Leu Ala Glu Glu Leu Met
        35                  40                  45
Arg Asn Gly Gln Leu Asp Asp Ser Ser Pro Leu Gly Lys Leu Leu Ala
    50                  55                  60
Lys Ser Met Ala Ala Asp Gly Lys Ala Gly Gly Gly Ile Glu Asp Val
65                  70                  75                  80
Ile Ala Ala Leu Asp Lys Leu Ile His Glu Lys Leu Gly Asp Asn Phe
                85                  90                  95
Gly Ala Ser Ala Asp Ser Ala Ser Gly Thr Gly Gln Gln Asp Leu Met
            100                 105                 110
Thr Gln Val Leu Asn Gly Leu Ala Lys Ser Met Leu Asp Asp Leu Leu
        115                 120                 125
Thr Lys Gln Asp Gly Gly Thr Ser Phe Ser Glu Asp Asp Met Pro Met
    130                 135                 140
Leu Asn Lys Ile Ala Gln Phe Met Asp Asp Asn Pro Ala Gln Phe Pro
145                 150                 155                 160
Lys Pro Asp Ser Gly Ser Trp Val Asn Glu Leu Lys Glu Asp Asn Phe
                165                 170                 175
Leu Asp Gly Asp Glu Thr Ala Ala Phe Arg Ser Ala Leu Asp Ile Ile
            180                 185                 190
Gly Gln Gln Leu Gly Asn Gln Gln Ser Asp Ala Gly Ser Leu Ala Gly
        195                 200                 205
Thr Gly Gly Gly Leu Gly Thr Pro Ser Ser Phe Ser Asn Asn Ser Ser
    210                 215                 220
Val Met Gly Asp Pro Leu Ile Asp Ala Asn Thr Gly Pro Gly Asp Ser
225                 230                 235                 240
Gly Asn Thr Arg Gly Glu Ala Gly Gln Leu Ile Gly Glu Leu Ile Asp
                245                 250                 255
Arg Gly Leu Gln Ser Val Leu Ala Gly Gly Gly Leu Gly Thr Pro Val
            260                 265                 270
Asn Thr Pro Gln Thr Gly Thr Ser Ala Asn Gly Gly Gln Ser Ala Gln
        275                 280                 285
Asp Leu Asp Gln Leu Leu Gly Gly Leu Leu Len Lys Gly Leu Gln Ala
    290                 295                 300
Thr Leu Lys Asp Ala Gly Gln Thr Gly Thr Asp Val Gln Ser Ser Ala
305                 310                 315                 320
Ala Gln Ile Ala Thr Len Len Vai Ser Thr Leu Leu Gln Gly Thr Arg
                325                 330                 335
Asn Gln Ala Ala Ala
            340
```

This hypersensitive response elicitor protein or polypeptide has a molecular weight of 34–35 kDa. It is rich in glycine (about 13.5%) and lacks cysteine and tyrosine. Further information about the hypersensitive response elicitor derived from Pseudomonas syringae is found in He, S. Y., et al., "*Pseudomonas syringae* pv. *syringae* Harpin$_{PSS}$: a Protein that is Secreted via the Hrp Pathway and Elicits the Hypersensitive Response in Plants," *Cell* 73:1255–1266 (1993), which is hereby incorporated by reference. The DNA molecule encoding this hypersensitive response elicitor from *Pseudomonas syringae* has a nucleotide sequence corresponding to SEQ. ID. No. 6 as follows:

```
atgcagagtc tcagtcttaa cagcagctcg ctgcaaaccc cggcaatggc ccttgtcctg     60

gtacgtcctg aagccgagac gactggcagt acgtcgagca aggcgcttca ggaagttgtc    120

gtgaagctgg ccgaggaact gatgcgcaat ggtcaactcg aogacagctc gccattggga    180

aaactgttgg ccaagtcgat ggccgcagat ggcaaggcgg gcggcggtat tgaggatgtc    240

atcgctgcgc tggacaagct gatccatgaa aagctcggtg acaacttcgg cgcgtctgcg    300

gacagcgcct cgggtaccgg acagcaggac ctgatgactc aggtgctcaa tggcctggcc    360

aagtcgatgc tcgatgatct tctgaccaag caggatggcg ggacaagctt ctccgaagac    420

gatatgccga tgctgaacaa gatcgcgcag ttcatggatg acaatcccgc acagtttccc    480

aagccggact cgggctcctg ggtgaacgaa ctcaaggaag acaacttcct tgatggcgac    540

gaaacggctg cgttccgttc ggcactcgac atcattggcc agcaactggg taatcagcag    600
```

-continued

```
agtgacgctg gcagtctggc agggacgggt ggaggtctgg gcactccgag cagtttttcc      660

aacaactcgt ccgtgatggg tgatccgctg atcgacgcca ataccggtcc cggtgacagc      720

ggcaataccc gtggtgaagc ggggcaactg atcggcgagc ttatcgaccg tggcctgcaa      780

tcggtattgg ccggtggtgg actgggcaca cccgtaaaca ccccgcagac cggtacgtcg      840

gcgaatggcg gacagtccgc tcaggatctt gatcagttgc tgggcggctt gctgctcaag      900

ggcctggagg caacgctcaa ggatgccggg caaacaggca ccgacgtgca gtcgagcgct      960

gcgcaaatcg ccaccttgct ggtcagtacg ctgctgcaag gcacccgcaa tcaggctgca     1020

gcctga                                                                1026
```

Another potentially suitable hypersensitive response elicitor from *Pseudomonas syringae* is disclosed in U.S. patent application Ser. No. 09/120,817, which is hereby incorporated by reference.

The hypersensitive response elicitor protein or polypeptide derived from *Pseudomonas solanacearum* has an amino acid sequence corresponding to SEQ. ID. No. 7 as follows:

```
Met Ser Val Gly Asn Ile Gln Ser Pro Ser Asn Leu Pro Gly Leu Gln
1               5                   10                  15
Asn Leu Asn Leu Asn Thr Asn Thr Asn Ser Gln Gln Ser Gly Gln Ser
            20                  25                  30
Val Gln Asp Leu Ile Lys Gln Val Glu Lys Asp Ile Leu Asn Ile Ile
        35                  40                  45
Ala Ala Leu Val Gln Lys Ala Ala Gln Ser Ala Gly Gly Asn Thr Gly
    50                  55                  60
Asn Thr Gly Asn Ala Pro Ala Lys Asp Gly Asn Ala Asn Ala Gly Ala
65                  70                  75                  80
Asn Asp Pro Sor Lys Asn Asp Pro Ser Lys Ser Gln Ala Pro Gln Ser
                85                  90                  95
Ala Asn Lys Thr Gly Asn Val Asp Asp Ala Asn Asn Gln Asp Pro Met
            100                 105                 110
Gln Ala Leu Met Gln Leu Leu Glu Asp Leu Val Lys Leu Leu Lys Ala
        115                 120                 125
Ala Leu His Met Gln Gln Pro Gly Gly Asn Asp Lys Gly Asn Gly Val
    130                 135                 140
Gly Gly Ala Asn Gly Ala Lys Gly Ala Gly Gly Gln Gly Gly Leu Ala
145                 150                 155                 160
Glu Ala Leu Gln Glu Ile Glu Gln Ile Leu Ala Gln Leu Gly Gly Gly
                165                 170                 175
Gly Ala Gly Ala Gly Gly Ala Gly Gly Gly Val Gly Gly Ala Gly Gly
            180                 185                 190
Ala Asp Gly Gly Ser Gly Ala Gly Gly Ala Gly Gly Ala Asn Gly Ala
        195                 200                 205
Asp Gly Gly Asn Gly Val Asn Gly Asn Gln Ala Asn Gly Pro Gln Asn
    210                 215                 220
Ala Gly Asp Val Asn Gly Ala Asn Gly Ala Asp Asp Gly Ser Glu Asp
225                 230                 235                 240
Gln Gly Gly Leu Thr Gly Val Leu Gln Lys Leu Met Lys Ile Leu Asn
                245                 250                 255
Ala Leu Val Gln Met Met Gln Gln Gly Gly Leu Gly Gly Gly Asn Gln
            260                 265                 270
Ala Gln Gly Gly Ser Lys Gly Ala Gly Asn Ala Ser Pro Ala Ser Gly
        275                 280                 285
Ala Asn Pro Gly Ala Asn Gln Pro Gly Ser Ala Asp Asp Gln Ser Ser
    290                 295                 300
Gly Gln Asn Asn Leu Gln Ser Gln Ile Met Asp Val Val Lys Glu Val
305                 310                 315                 320
Val Gln Ile Leu Gln Gln Met Leu Ala Ala Gln Asn Gly Gly Ser Gln
                325                 330                 335
Gln Ser Thr Ser Thr Gln Pro Met
            340
```

Further information regarding this hypersensitive response elicitor protein or polypeptide derived from *Pseudomonas solanacearum* is set forth in Arlat, M., et al., "PopA1, a Protein which Induces a Hypersensitive-like Response in Specific Petunia Genotypes, is Secreted via the Hrp Pathway of *Pseudomonas solanacearum,*" *EMBO J.* 13:543–533 (1994), which is hereby incorporated by reference. It is encoded by a DNA molecule from *Pseudomonas solanacearum* having a nucleotide sequence corresponding SEQ. ID. No. 8 as follows:

```
atgtcagtcg gaaacatcca gagcccgtcg aacctcccgg gtctgcagaa cctgaacctc        60
aacaccaaca ccaacagcca gcaatcgggc cagtcc9tgc aagacctgat caagcaggtc 120
gagaaggaca tcctcaacat catcgcagcc ctcgtgcaga aggccgcaca gtcggcgggc 180
ggcaacaccg gtaacaccgg caacgcgccg gcgaaggacg gcaatgccaa cgcgggcgcc 240
aacgacccga gcaagaacga cccgagcaag agccaggctc cgcagtcggc caacaagacc 300
ggcaacgtcg acgacgccaa caaccaggat ccgatgcaag cgctgatgca gctgctggaa 360
gacctggtga agctgctgaa ggcggccctg cacatgcagc agcccggcgg caatgacaag 420
ggcaacggcg tgggcggtgc caacggcgcc aagggtgccg gcggccaggg cggcctggcc 480
gaagcgctgc aggagatcga gcagatcctc gcccagctcg gcggcggcgg tgctggcgcc 540
ggcggcgcgg gtggcggtgt cggcggtgct ggtggcgcgg atggcggctc cggtgcgggt 600
ggcgcaggcg gtgcgaacgg cgccgacggc ggcaatggcg tgaacggcaa ccaggcgaac 660
ggcccgcaga acgcaggcga tgtcaacggt gccaacggcg cggatgacgg cagcgaagac 720
cagggcggcc tcaccggcgt gctgcaaaag ctgatgaaga tcctgaacgc gctggtgcag 780
atgatgcagc aaggcggcct cggcggcggc aaccaggcgc agggcggctc gaagggtgcc 840
ggcaacgcct cgccggcttc cggcgcgaac ccgggcgcga accagcccgg ttcggcggat 900
gatcaatcgt ccggccagaa caatctgcaa tcccagatca tggatgtggt gaaggaggtc 960
gtccagatcc tgcagcagat gctggcggcg cagaacggcg gcagccagca gtccacctcg 1020
acgcagccga tgtaa                                                 1035
```

Other embodiments of the present invention include, but are not limited to, use of the nucleotide sequence encoding for the hypersensitive response elicitor protein or polypeptide from *Erwinia carotovora* and *Erwinia stewartii*. Isolation of *Erwinia carotovora* hypersensitive response elicitor protein or polypeptide is described in Cui, et al., "The RsmA Mutants of *Erwinia carotovora* subsp. *carotovora* Strain Ecc71 Overexpress hrp $N_{Ecc}$ and Elicit a Hypersensitive Reaction-like Response in Tobacco Leaves," *MPMI,* 9(7): 565–73 (1996), which is hereby incorporated by reference. The hypersensitive response elicitor protein or polypeptide of *Erwinia stewartii* is set forth in Ahmad, et al., "Harpin is Not Necessary for the Pathogenicity of *Erwinia stewartii* on Maize," *8th Int'l. Cong. Molec. Plant-Microbe Interact.*, Jul. 14–19, 1996 and Ahmad, et al., "Harpin is Not Necessary for the Pathogenicity of *Erwinia stewartii* on Maize," *Ann. Mtg. Am. Phytopath. Soc.*, Jul. 27–31, 1996, which are hereby incorporated by reference.

The hypersensitive response elicitor proteins or polypeptides from various *Phytophora* species are described in Kaman, et al., "Extracellular Protein Elicitors from *Phytophthora*: Most Specificity and Induction of Resistance to Bacterial and Fungal Phytopathogens," *Molec. Plant-Microbe Interact.,* 6(1):15–25 (1993); Ricci, et al., "Structure and Activity of Proteins from Pathogenic Fungi *Phytophthora* Eliciting Necrosis and Acquired Resistance in Tobacco," *Eur. J. Biochem.,* 183:555–63 (1989); Ricci, et al., "Differential Production of Parasiticein, and Elicitor of Necrosis and Resistance in Tobacco, by Isolates of *Phytophthora parasitica,*" *Plant Path.* 41:298–307 (1992); Baillreul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *Plant J.,* 8(4): 551–60 (1995), and Bonnet, et al., "Acquired Resistance Triggered by Elicitors in Tobacco and Other Plants," *Eur. J. Plant Path.,* 102:181–92 (1996), which are hereby incorporated by reference.

Another hypersensitive response elicitor in accordance with the present invention is from *Clavibacter michiganensis* subsp. *sepedonicus* which is described in U.S. patent application Ser. No. 09/136,625, which is hereby incorporated by reference.

Other elicitors can be readily identified by isolating putative hypersensitive response elicitors and testing them for elicitor activity as described, for example, in Wei, Z-M., et al., "Harpin, Elicitor of the Hypersensitive Response Produced by the Plant Pathogen *Erwinia amylovora,*" *Science* 257:85–88 (1992), which is hereby incorporated by reference. Cell-free preparations from culture supernatants can be tested for elicitor activity (i.e., local necrosis) by using them to infiltrate appropriate plant tissues. Once identified, DNA molecules encoding a hypersensitive response elicitor can be isolated using standard techniques known to those skilled in the art. The isolated DNA molecule can then be introduced into the chimeric gene for expression in a transgenic plant of the present invention.

The first DNA molecule can also encode fragments of the above hypersensitive response elicitor proteins or polypeptides as well as fragments of full length elicitors from other pathogens.

Suitable fragments can be produced by several means. Subclones of the gene encoding a known elicitor protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), which are hereby incorporated by reference. The subclones then are expressed in vitro or in vivo in bacterial cells to yield a smaller protein or polypeptide that can be tested for elicitor activity, e.g., using procedures set forth in Wei, Z-M., et al., *Science* 257: 85–88 (1992), which is hereby incorporated by reference.

In another approach, based on knowledge of the primary structure of the protein, fragments of the elicitor protein gene may be synthesized using the PCR technique together with specific sets of primers chosen to represent particular portions of the protein. Erlich, H. A., et al., "Recent Advances in the Polymerase Chain Reaction," *Science* 252: 1643–51 (1991), which is hereby incorporated by reference. These can then be cloned into an appropriate vector for expression of a truncated protein or polypeptide from bacterial cells as described above.

An example of suitable fragments of a hypersensitive response elicitor which elicit a hypersensitive response are fragments of the *Erwinia amylovora* hypersensitive response elicitor protein or polypeptide of SEQ. ID. No. 3. The fragments can be a C-terminal fragment of the amino acid sequence of SEQ. ID. No. 3, an N-terminal fragment of the amino acid sequence of SEQ. ID. No. 3, or an intern al fragment of the amino acid sequence of SEQ. ID. No. 3. The C-terminal fragment of the amino acid sequence of SEQ. ID. No. 3 can span amino acids 105 and 403 of SEQ. ID. No. 3. The N-terminal fragment of the amino acid sequence of SEQ. ID. No. 3 can span the following amino acids of SEQ. ID. No. 3: 1 and 98, 1 and 104, 1 and 122, 1 and 168, 1 and 218, 1 and 266, 1 and 342, 1 and 321, and 1 and 372. The internal fragment of the amino acid sequence of SEQ. ID. No. 3 can span the following amino acids of SEQ. ID. No. 3: 76 and 209, 105 and 209,99 and 209, 137 and 204, 137 and 200, 109 and 204, 109 and 200, 137 and 180, and 105 and 180. DNA molecules encoding these fragments can also be utilized in the chimeric gene of the present invention.

The first DNA molecule also can be a DNA molecule that hybridizes under stringent conditions to the DNA molecule having nucleotide sequence of SEQ. ID. Nos. 2, 4, 6, or 8. An example of suitable stringency conditions is when hybridization is carried out at a temperature of about 37° C. using a hybridization medium that includes 0.9M sodium citrate ("SSC") buffer, followed by washing with 0.2×SSC buffer at 37° C. Higher stringency can readily be attained by increasing the temperature for either hybridization or washing conditions or increasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 42° C. to about 65° C. for up to about 20 hours in a hybridization medium containing 1 M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 μg/ml *E. coli* DNA, followed by washing carried out at between about 42° C. to about 65° C. in a 0.2×SSC buffer.

Variants of suitable hypersensitive response elicitor proteins or polypeptides can also be expressed by the first DNA molecule. Variants may be made by, for example, the deletion, addition, or alteration of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide (such as a 6×His tag).

The promoter of the chimeric gene should be selected on the basis of its ability to induce transcription of the first DNA molecule in response to infection of the plant by an oomycete (i.e., the oomycete activates the promoter). According to one embodiment, the promoter preferably includes some or all of the promoter-effective regions of a gst1 gene from potato. The gst1 promoter is activated in response to infection by oomycetes and not by wounding or other environmental perturbations. The gst1 promoter from potato has a nucleic acid sequence corresponding to SEQ. ID. No. 9 as follows:

```
gaattcagga agaattttgt aggttcaact aaattatata tatatatata aaaaaataaa      60

aattattaga cgcttcgact atttacttac tttaaaattt gaattttcgt acgaataaaa     120

ttatttgtca gagaaaagtc ttttagctat tcacatgcta ggaagtttca cttttggtgg     180

atcagtgatt gtatattatt taatatatat caattttctc atcaaactga aaatgaaaga     240

taaaattaat attaaaaact ccattcattt taatttattg tcatgttttg acttgatcca     300

aaatctaaca atttaaaagg ttttaaattt ttgtgctttt ttttaaatta aaaatatgtc     360

aaatatatta aaatatattt tttaaatttt atactaaaaa acatgtcaca tgaatatttg     420

aaattataaa attatcaaaa ataaaaaaag aatatttctt taacaaatta aaattgaaaa     480

tatgataaat aaattaaact attctatcat tgatttttct agccaccaga tttgaccaaa     540

cagtgggtga catgagcaca taagtcatct ttattgtatt ttattactca ctccaaaaat     600
```

-continued

```
atagggaata tgtttactac ttaatttagt caaatataat tttatattag aataattgaa        660

tagtcaaaca agaaacttta atgcatcctt attttt                                  696
```

Effective fragments of SEQ. ID. No. 9 are also encompassed by the present invention. U.S. Pat. Nos. 5,750,874 and 5,723,760 to Strittmayer et al., which are hereby incorporated by reference, define promoter-effective regions of the potato gst1 promoter. Preferably, the gst1 promoter includes a nucleotide sequence corresponding, at a minimum, to nucleotides 295–567 of SEQ. ID. No. 9. The gst1 promoter can also include effective portions containing nucleotides 295–696 of SEQ. ID. No. 9.

The chimeric gene of the present invention also includes an operable 3' regulatory region, selected from among those which are capable of providing correct transcription termination and polyadenylation of mRNA for expression in plant cells, operably linked to the first DNA molecule which encodes for a hypersensitive response elicitor. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l Acad. Sci. USA,* 80:4803–4807 (1983), which is hereby incorporated by reference) and the cauliflower mosaic virus 3' regulatory region (Odell, et al., "Identification of DNA Sequences Required for Activity of the Cauliflower Mosaic Virus 35S Promoter," *Nature,* 313(6005):810–812 (1985), which is hereby incorporated by reference). Virtually any 3' regulatory region known to be operable in plants would suffice for proper expression of the coding sequence of the chimeric gene of the present invention.

The first DNA molecule, promoter, and a 3' regulatory region can be ligated together using well known molecular cloning techniques described in Sambrook et al., *Molecular Cloning: A Laboratory Manual*, Second Edition, Cold Spring Harbor Press, N.Y. (1989), which is hereby incorporated by reference.

The chimeric gene can also include a second DNA molecule encoding a secretion signal. A number of suitable secretion signals are known in the art and other are continually being identified. The secretion signal can be an RNA leader which directs secretion of the subsequently transcribed protein or polypeptide, or the secretion signal can be an amino terminal peptide sequence that is recognized by a host plant secretory pathway. The second DNA molecule can be ligated between the promoter and the first DNA molecule, using known molecular cloning techniques as indicated above.

According to one embodiment, the second DNA molecule encodes a secretion signal derived from *Nicotiana tabacum*. Specifically, this DNA molecule encodes the secretion signal polypeptide for PR1-b gene of *Nicotiana tabacum*. This second DNA molecule has a nucleotide sequence corresponding to SEQ. ID. No. 10 as follows:

```
tctagaccat gggatttttt ctcttttcac aaatgccctc atttttttctt gtgtcgacac        60

ttctcttatt cctaataata tctcactctt ctcatgccca aaactctaga                   110
```

The above sequence includes XbaI sites (underlined) at each end to facilitate insertion of the second DNA molecule into the chimeric gene of the present invention. The coding sequence of SEQ. ID. No. 10 starts at base 8. The polypeptide encoded by this nucleic acid molecule has an amino acid sequence corresponding to SEQ. ID. No. 11 as follows:

```
Met Gly Phe Phe Leu Phe Ser Gln Met Pro Ser Phe Phe Leu Val Ser
  1               5                  10                  15

Thr Leu Leu Leu Phe Leu Ile Ile Ser His Ser Ser His Ala Gln Asn
             20                  25                  30

Ser Arg
```

An alternative second DNA molecule encoding the secretion signal polypeptide for PR1-B gene of *Nicotiana tabacum* has a nucleotide sequence corresponding to SEQ. ID. No. 12 as follows:

```
atgggatttt ttctcttttc acaaatgccc tcattttttc ttgtctctac acttctctta   60

ttcctaataa tatctcactc ttctcatgcc caaaactctc aa                      102
```

This nucleotide sequence is disclosed in Genbank Accession No. X03465, which is hereby incorporated by reference. The polypeptide encoded by this nucleic acid molecule has an amino acid sequence corresponding to SEQ. ID. No. 13 as follows:

```
Met Gly Phe Phe Leu Phe Ser Gln Met Pro Ser Phe Phe Leu Val Ser
  1             5                  10                  15

Thr Leu Leu Leu Phe Leu Ile Ile Ser His Ser Ser His Ala Gln Asn
             20                  25                  30

Ser Gln
```

Yet another second DNA molecule encodes the secretion signal for the PR1-a gene of *Nicotiana tabacum*. This DNA molecule has a nucleotide sequence corresponding to SEQ. ID. No. 14 as follows:

```
atgggatttg ttctcttttc acaattgcct tcatttcttc ttgtctctac acttctctta  60

ttcctagtaa tatcccactc ttgccgtgcc                                    90
```

This DNA molecule is disclosed in Genbank Accession No. X06361, which is hereby incorporated by reference. The polypeptide encoded by this nucleic acid molecule has an amino acid sequence corresponding to SEQ. ID. No. 15 as follows:

```
Met Gly Phe Val Leu Phe Ser Gln Leu Pro Ser Phe Leu Leu Val Ser
  1             5                  10                  15

Thr Leu Leu Leu Phe Leu Val Ile Ser His Ser Cys Arg Ala
             20                  25                  30
```

Still another second DNA molecule encodes the secretion signal for the PR4-a gene of *Nicotiana tabacum*. This DNA molecule has a nucleotide sequence corresponding to SEQ. ID. No. 16 as follows:

```
atggagagag ttaataatta taagttgtgc gtggcattgt tgatcatcag catggtgatg  60

gcaatggcgg cggca                                                    75
```

This DNA molecule is disclosed in Genbank Accession No. X58546, which is hereby incorporated by reference. The polypeptide encoded by this nucleic acid molecule has an amino acid sequence corresponding to SEQ. ID. No. 17 as follows:

```
Met Glu Arg Val Asn Asn Tyr Lys Leu Cys Val Ala Leu Leu Ile Ile
  1             5                  10                  15

Ser Met Val Met Ala Met Ala Ala Ala
             20                  25
```

Each second DNA molecule can be cloned using primers that introduce restriction sites at the 5' and 3' ends thereof to facilitate insertion of the second DNA molecule into the chimeric gene of the present invention. SEQ. ID. No. 10 is shown to include such restriction sites (e.g., XbaI).

Further aspects of the present invention include an expression system that includes a vector containing a chimeric gene of the present invention, as well as a host cell which includes a chimeric gene of the present invention. As described more fully hereinafter, the recombinant host cell can be either a bacterial cell (i.e., *Agrobacterium*) or a plant cell. In the case of recombinant plant cells, it is preferable that the chimeric gene is stably inserted into the genome of the recombinant plant cell.

The chimeric gene can be incorporated into cells using conventional recombinant DNA technology. Generally, this involves inserting the chimeric gene into an expression vector or system to which it is heterologous (i.e., not normally present). As described above, the chimeric gene contains the necessary elements for the transcription and translation in plant cells of the first DNA molecule (i.e., encoding the hypersensitive response elicitor protein or polypeptide) and, if present, the second DNA molecule.

U.S. Pat. No. 4,237,224 issued to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Once the chimeric gene of the present invention has been prepared, it is ready to be incorporated into a host cell.

Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Springs Laboratory, Cold Springs Harbor, N.Y. (1989), which is hereby incorporated by reference. Suitable host cells include, but are not limited to, bacteria, virus, yeast, mammalian cells, insect, plant, and the like. Preferably the host cells are either a bacterial cell or a plant cell.

Accordingly, another aspect of the present invention relates to a method of making a recombinant plant cell. Basically, this method is carried out by transforming a plant cell with a chimeric gene of the present invention under conditions effective to yield transcription of the first DNA molecule in response to oomycete-induced activation of the promoter. Preferably, the chimeric gene is stably inserted into the genome of the recombinant plant cell as a result of the transformation.

A related aspect of the present invention concerns a method of making a plant resistant to disease resulting from oomycete infection. Basically, this method is carried out by transforming a plant cell with a chimeric gene of the present invention under conditions effective to yield transcription of the first DNA molecule in response to oomycete-induced activation of the promoter and regenerating a plant from the transformed plant cell.

One approach to transforming plant cells with a chimeric gene of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036, 006, and 5,100,792, all to Sanford, et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Another method of introducing the chimeric gene is fusion of protoplasts with other entities, either minicells, cells, lysosomes, or other fusible lipid-surfaced bodies that contain the chimeric gene. Fraley, et al., *Proc. Natl. Acad. Sci. USA,* 79:1859–63 (1982), which is hereby incorporated by reference.

The chimeric gene may also be introduced into the plant cells by electroporation. Fromm, et al., *Proc. Natl. Acad. Sci. USA,* 82:5824 (1985), which is hereby incorporated by reference. In this technique, plant protoplasts are electroporated in the presence of plasmids containing the chimeric gene. Electrical impulses of high field strength reversibly permeabilize biomembranes allowing the introduction of the plasmids. Electroporated plant protoplasts reform the cell wall, divide, and regenerate.

Another method of introducing the chimeric gene into plant cells is to infect a plant cell with *Agrobacterium tumefaciens* or *Agrobacterium rhizogenes* previously transformed with the chimeric gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

*Agrobacterium* is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences such as a chimeric gene of the present invention can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. Schell, J., *Science,* 237:1176–83 (1987), which is hereby incorporated by reference.

Plant tissue suitable for transformation include leaf tissue, root tissue, meristems, zygotic and somatic embryos, and anthers.

After transformation, the transformed plant cells can be selected and regenerated.

Preferably, transformed cells are first identified using, e.g., a selection marker simultaneously introduced into the host cells along with the chimeric gene of the present invention. Suitable selection markers include, without limitation, markers coding for antibiotic resistance, such as kanamycin resistance (Fraley, et al., *Proc. Natl. Acad. Sci. USA,* 80:4803–4807 (1983), which is hereby incorporated by reference). A number of antibiotic-resistance markers are known in the art and other are continually being identified. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow.

Once a recombinant plant cell or tissue has been obtained, it is possible to regenerate a full-grown plant therefrom. Thus, another aspect of the present invention relates to a transgenic plant that is resistant to disease resulting from oomycete infection. The transgenic plant includes a chimeric gene of the present invention, wherein the promoter induces transcription of the first DNA molecule in response to infection of the plant by an oomycete. Preferably, the chimeric gene is stably inserted into the genome of the transgenic plant of the present invention.

Plant regeneration from cultured protoplasts is described in Evans, et al., *Handbook of Plant Cell Cultures*, Vol. 1: (MacMillan Publishing Co., New York, 1983); and Vasil I. R. (ed.), *Cell Culture and Somatic Cell Genetics of Plants*, Acad. Press, Orlando, Vol. 1, 1984, and Vol. III (1986), which are hereby incorporated by reference.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the chimeric gene is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

Resistance against different types of oomycetes may be imparted to transgenic plants according to the present invention. Without being bound by any particular theory, it is believed that a hypersensitive response elicitor protein or polypeptide encoded by the first DNA molecule is transcribed in response to infection of the plant by an oomycete. The exact mechanism by which the promoter is activated to regulate transcription of sequences under its control is not fully understood; however, the first DNA molecule is transcribed and the hypersensitive response elicitor is expressed in a limited population of cells (i.e., those in which transcription has been induced following oomycete infection). Once expressed, it is believed that the hypersensitive response elicitor can either be secreted from the plant cell (assuming the chimeric gene also contains a second DNA molecule encoding an N-terminal secretion signal) or leaked from an oomycete-infected plant cell. Regardless of how the hypersensitive response elicitor is delivered to the intercellular environment, it is believed that the hypersensitive response elicitor protein or polypeptide will initiate a hypersensitive response to cause localized necrosis of oomycete-infected tissues. In addition, systemic acquired resistance may be developed by the transgenic plant following initiation of the hypersensitive response. This may yield broad disease and/or pathogen resistance to the transgenic plants of the present invention.

Oomycetes against which resistance is imparted include, without limitation, species of *Plasmopara, Phytophthora, Peronospora, Pseudoperonospora, Bremia, Sclerospora, Aphanomyces, Pythium*, and *Albugo*.

According to one embodiment of the present invention, an oomycete resistant transgenic tobacco plant includes a chimeric gene of the present invention, wherein expression of the encoded hypersensitive response elicitor is responsive to infection of the plant by an oomycete that is a pathogen of tobacco, including, but not limited to, *Peronospora tabacina* (which causes blue mold) and *Phyophthora parasitica* (which causes black shank).

The chimeric gene of the present invention can be utilized to impart oomycete resistance for a wide variety of tobacco plants, some of which may possess varying levels of natural resistance against pathogenic oomycetes. The varieties of tobacco plants which can be protected include, without limitation, those referred to as Coker 371 Gold, K 149, K 326, K 346, K 394, K 730, RG 11, RG17, RG22, Speight G-70, Speight G-117, Speight G-126, GL939, NC 55, NC 71, NC 72, NC 95, NC 2326, OX 207, OX 940, RG 81, RG H4, RG H61, Speight 168, SpeightNF3, Speight 172, CU 236, CU 387, CU 368, NC TG91, OX 4142NF, OX 4083, RG 4H2-12, RG 4H2-17, RG 4H2-20, Speight 177, Speight 178, Speight 179, VPI 107, VPI 605, NG TG94, KY 14, KY 8959, KY 907, KY 908, TN 86, TN 90, TN 97, VA 116, VA 509, B 21×KY 10, KY 14×L8, NC 3, NC BH129, DH332, COOP 313, COOP 543, Clay's 403, Clay's 502, HY 402, PF 561, and R 711.

According to another embodiment of the present invention, an oomycete resistant transgenic grape plant includes a chimeric gene of the present invention, wherein expression of the encoded hypersensitive response elicitor is responsive to infection of the plant by an oomycete that is a pathogen of grape, including, but not limited to, *Plasmopara viticola* (which causes downy mildew), *Pythium* spp. (which cause root and/or stem rot), and *Phytophthora* spp. (which cause root and/or stem rot).

The chimeric gene of the present invention can be utilized to impart oomycete resistance for a wide variety of grapevine plants. The chimeric gene is particularly well suited to imparting resistance to *Vitis* scion or rootstock cultivars. Scion cultivars which can be protected include, without limitation, those commonly referred to as Table or Raisin Grapes, such as Alden, Almeria, Anab-E-Shahi, Autumn Black, Beauty Seedless, Black Cornish, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include, without limitation, those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel. Rootstock cultivars which can be protected include Couderc 1202, Couderc 1613, Couderc 1616, Couderc 3309, Dog Ridge, Foex 33 EM, Freedom, Ganzin 1 (A×R #1), Harmony, Kober 5BB, LN33, Millardet & de Grasset 41B, Millardet & de Grasset 420A, Millardet & de Grasset 101–14, Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, Vitis rupestris Constantia, *Vitis california*, and *Vitis girdiana.*

Once transgenic plants of this type are produced, the plants themselves can be cultivated in accordance with conventional procedures. Alternatively, transgenic seeds or propagules (e.g., scion or rootstock cultivars) are recovered from the transgenic plants. The seeds can then be planted in the soil and cultivated using conventional procedures to produce transgenic plants. The transgenic plants are propagated from the planted transgenic seeds under conditions effective to impart oomycete resistance to plants.

EXAMPLES

The following examples are provided to illustrate embodiments of the present invention, but they are by no means intended to limit its scope.

Example 1

Construction of Chimeric Gene

Cloning of gst1 Promoter

The gst1 promoter region from nucleotides (539 to +48) (Martini et al., "Promoter Sequences of a Potato Pathogenesis-related Gene Mediate Transcriptional Activation Selectively upon Fungal Infection," *Mol. Gen. Genet.* 236 (2–3): 179–86 (1993), which is hereby incorporated by reference), was PCR amplified using DNA from potato cultivar Atlantic, using a forward primer containing a BamHI site (SEQ. ID. No. 18) as follows:

```
tgacggatcc taggaagttt cacttttggt gg          32
```

a reverse primer containing an EcoRI site (SEQ. ID. No. 19) as follows:

```
tagcgaattc tatgtgtggt tggtctccct tg          32
```

and PrimeZyme DNA polymerase (Whatman Biometra, Goettingen, Germany). The DNA was ligated into the LITMUS 38 vector (New England Biolabs, Beverly, Mass.) and three clones were sequenced on an ABI 377 sequencer at the Cornell BioResource Center. Each clone had two to three nucleotide changes when compared to the published sequence (Martini et al., "Promoter Sequences of a Potato Pathogenesis-related Gene Mediate Transcriptional Activation Selectively upon Fungal Infection," *Mol. Gen. Genet.* 236: (2–3) 179–86 (1993), which is hereby incorporated by reference). The changes were most likely due to mistakes made by the polymerase because the promoter is extremely A-T rich and all but one of the changes were in different places in the three clones. One clone, pCPP1308, with a single change in the cis-acting region identified by Martini et al. ("Promoter Sequences of a Potato Pathogenesis-related Gene Mediate Transcriptional Activation Selectively upon Fungal Infection," *Mol. Gen. Genet.* 236: (2–3) 179–86 (1993), which is hereby incorporated by reference) was used as the source of the gst1 promoter in all subsequent constructions.

Plant Transformation Constructs

The gst1:uidA construct was made by ligating the gst1 promoter from pCPP1308 into pBI101 (Clontech Labs, Palo Alto, Calif.). For the gst1:hrpN and gst1:signal sequence: hrpN constructs (described below), the gst1 promoter region was engineered to have a 5' HindIII site and a 3' XbaI site by the polymerase chain reaction (PCR) using pCPP1308 as the template. The forward primer had the nucleotide sequence of SEQ. ID. No. 18 and the reverse primer had a nucleotide sequence according to SEQ. ID. No. 20 as follows:

```
tacgtctaga tatgtgtggt tggtctccct tg          32
```

For gst1:hrpN constructs, the hrpN gene of *Erwinia amylovora* (i.e., encoding a hypersensitive response elicitor identified as harpinea) was engineered to have a 5' XbaI restriction site and a 3' SstI restriction site by PCR using pCPP1084 (Wei et al., "Harpin, Elicitor of the Hypersensitive Response Produced by the Plant Pathogen *Erwinia Amylovora,*" *Science* 257:85–88 (1992), which is hereby incorporated by reference) as the template. The forward primer had a nucleotide sequence corresponding to SEQ. ID. No. 21 as follows:

```
atactctaga accatgggtc tgaatacaag tggg        34
```

and the reverse primer had a nucleotide sequence corresponding to SEQ. ID. No. 22 as follows:

```
tcatgagctc ttaagccggc ccagcttgcc aagtg   35
```

For gst1:signal sequence:hrpN, the hrpN gene was engineered to have a BamHI site on each end. The forward primer had a nucleotide sequence corresponding to SEQ. ID. No. 23 as follows:

```
tagaggatcc ctgaatacaa gtgggctggg agcg  34
```

and the reverse primer had a nucleotide sequence corresponding to SEQ. ID. No. 24 as follows:

```
tcatggatcc ttaagccgcg cccagcttgc caagtg   36
```

The nopaline synthase terminator was extracted from pBI101 by digesting with SstI and EcoRI.

The nucleic acid molecule encoding the PR1-b signal sequence (of SEQ. ID. No. 1) was engineered to have XbaI restriction sites on both ends. The forward primer had a nucleotide sequence corresponding to SEQ. ID. No. 25 as follows:

```
atactctaga ccatgggatt ttttctcttt tca       33
```

and the reverse primer had a nucleotide sequence corresponding to SEQ. ID. No. 26 as follows:

```
aggtctagag ttttgggcat gagaagagtg       30
```

The fragment was amplified using pSKG55 as a template (Gopalan et al., "Expression of the Pseudomonas Syringae Avirulence Protein AvrB in Plant Cells Alleviates its Dependence on the Hypersensitive Response and Pathogenicity (Hrp) Secretion System in Elicitating Genotype-Specific Hypersensitive Cell Death." *Plant Cell* 8:1095–1105 (1996), which is hereby incorporated by reference).

PrimeZyme DNA polymerase (Whatman Biometra, Goettingen, Germany) was used with a hot start procedure for amplification of all fragments. The amplified fragments were purified, digested with the appropriate enzymes, and ligated into the binary vector pPZP221 (Hajdukiewicz et al., "The Small Versatile pPZP Family of *Agrobacterium* Binary Vectors for Plant Transformation," *Plant Mol. Bio.* 25:989–994 (1994), which is hereby incorporated by reference) or intermediate constructs, to build up the final constructs. The proper construction of pCPP1294 (FIG. 1) was confirmed by sequencing on an ABI 377 automated sequencer.

The final constructs were transformed into *Agrobacterium tumefaciens* strain GV3101 (Martin et al., "The GUS Reporter System as a Tool to Study Plant Gene Expression," in Gallagher, ed., *GUS Protocols: Using the GUS Gene as a Reporter of Gene Expression*, Academic Press, pp. 23–43 (1992), which is hereby incorporated by reference) by electroporation using a Bio-Rad GenePulser (Bio-Rad Ltd., York, UK).

Example 2

Inoculation With *Peronospora parasitica* Activates gst1 Transcription in *Arabidopsis*

To evaluate the activity of the gst1 promoter in a plant other than potato, transgenic *Arabidopsis* were constructed containing the *E. coli* uidA gene for β-glucuronidase (GUS) under control of the gst1 promoter. Histochemical GUS assays of were performed essentially as described by Martin et al., "The GUS Reporter System as a Tool to Study Plant Gene Expression," in Gallagher, ed., *GUS Protocols: Using the GUS Gene as a Reporter of Gene Expression*, Academic Press, pp. 23–43 (1992), which is hereby incorporated by reference. Uninoculated and inoculated whole small *Arabidopsis* plants were submerged for 30 minutes on ice in six well microtiter plates in a solution of 1.5% freshly prepared paraformaldehyde in 100 mM sodium phosphate buffer, pH 7.2, containing 0.1% Triton X-100. The plants were washed twice for 5 minutes with sodium phosphate buffer pH 7.2. The plants were then submerged in a solution of 2 mM X-gluc (5-bromo-4-chloro-3-indolyl β-D-glucuronide), 50 mM sodium phosphate, pH 7.2, 0.5% Triton X-100. The solution was vacuum infiltrated into the plants and the plants were then incubated for 16 hours in the dark at 37° C. The staining was stopped by rinsing the plants several times in water and the tissue was then cleared by incubating in several changes of 70% ethanol.

Figure 2:
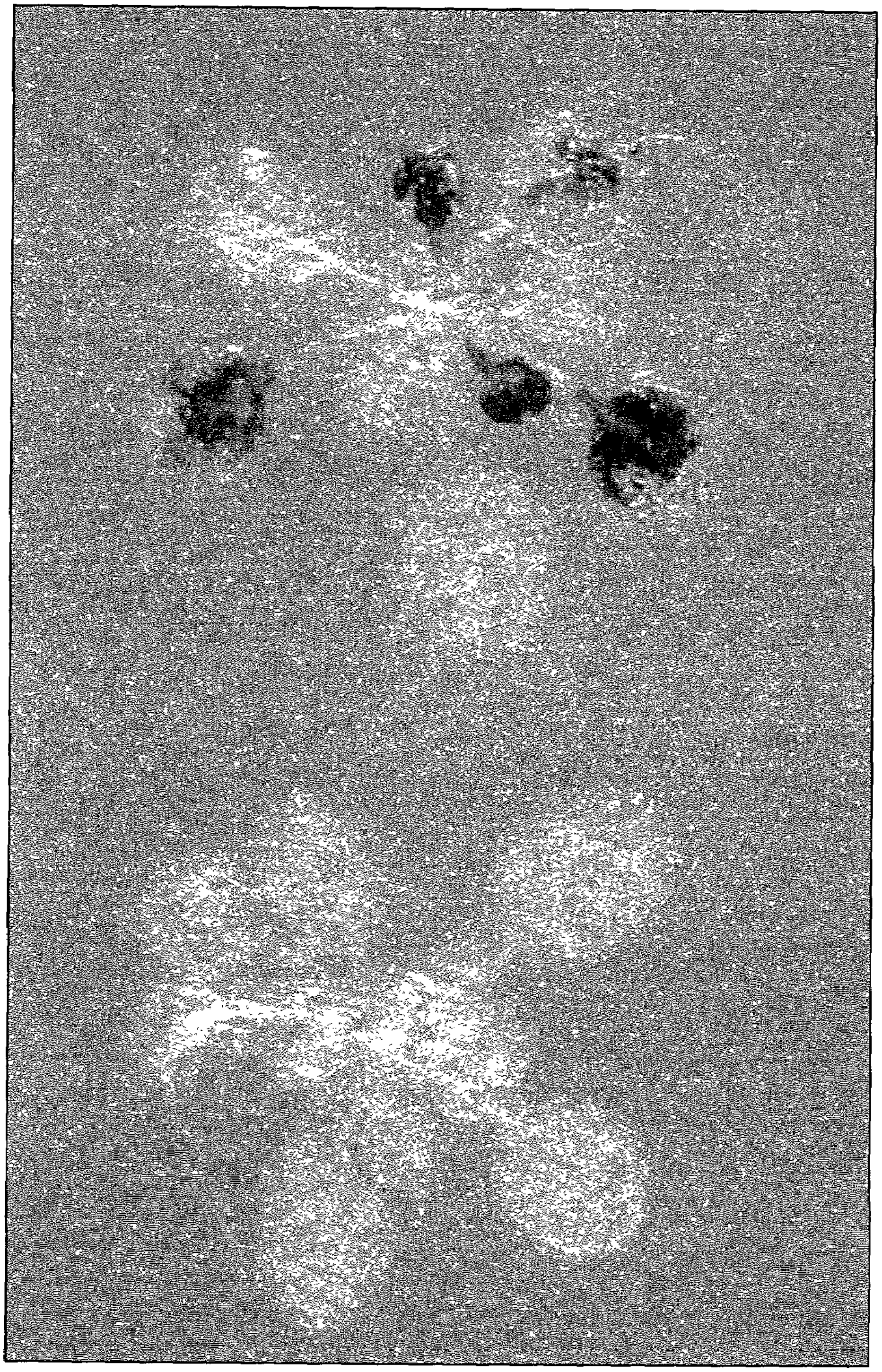
FIG. 2 is an image of transgenic *Arabidopsis* plants containing a construct encoding GUS under control of the gst1 promoter. To demonstrate pathogen inducibility of the gst1 promoter in *Arabidopsis*, GUS staining was measured following inoculation of the plants with water (left) or *P. parasitica* (right). GUS expression is indicated by dark staining.

Twenty lines were evaluated for GUS expression in uninoculated leaves, leaves inoculated with *Peronospora parasitica* isolate NOCO, and whole plants using a histochemical staining procedure (Martin et al., "The GUS Reporter System as a Tool to Study Plant Gene Expression," in Gallagher, ed., *GUS Protocols: Using the GUS Gene as a Reporter of Gene Expression*, Academic Press, pp 23–43 (1992), which is hereby incorporated by reference). Five lines showed more intense staining of the inoculated areas than the uninoculated areas and two lines showed no visible staining of any plant parts except the inoculated leaves (FIG. 2). These results are consistent with those reported for potato and reveal that the gst1 promoter is pathogen inducible in *Arabidopsis*. No induction of GUS activity was detected in the five lines that responded to *P. parasitica* when inoculated with *Pseudomonas syringae* pv. tomato strain DC3000, even after disease symptoms appeared (results not shown). Previously, it was reported that the gst1 gene is induced in response to fungi, viruses, and nematodes (Strittmatter et al., "Infections with Various Types of Organisms Stimulate Transcription From a Short Promoter Fragment of the Potato Gst1 Gene," *Mol. Plant-Microbe Interact.* 9:68–73 (1996), which is hereby incorporated by reference), but results with bacterial pathogens were not reported.

Example 3

Pathogen Inducible Expression of hrpN in Transgenic *Arabidopsis*

To generate transgenic *Arabidopsis* expressing hrpN in a pathogen-inducible manner, plant transformation vectors, pCPP 1292 for cytoplasmic localization of HrpN in plants, and pCPP 1294 for extracellular localization of HrpN, were constructed. (FIGS. 3A and 3B). *Arabidopsis* ecotype Columbia (Col-O) was transformed with the two constructs. *Arabidopsis thaliana* ecotype Columbia (Col-O) plants were grown in a growth chamber at 22° C. and a 17 hour photoperiod. Plants with primary fluorescence 5–15 cm tall were transformed via a known vacuum infiltration method (protocol available from *Dr. Pamela Green of Michigan State University* adapted from Bechtold et al., *C. R. Acad. Sci.* Paris 316:1194–1199 (1993), and Bent et al., *Science* 237:1856–1860 (1994), which are hereby incorporated by reference. Seeds were collected from each plant individually, sterilized and spread on selection plates containing 150 mg/l gentamycin, 0.2 g/l *Arabidopsis* Growth Medium (Lehie Seeds), and 0.7% Phytagar (Gibco BRL, Bethesda, MD). Plates were vernalized for 2 days at 4° C. and then moved to a growth chamber maintained at 22° C. and 14 hours light. Gentamycin resistant plants were selected after 2 weeks and individual plants were transplanted to soil. Each individual T1 seedling was brought up by single seed descent and individual plant lines were selected for lack of segregation of gentamycin resistance in the T3 generation. Insertion of T-DNA was confirmed by PCR and Southern analysis.

Transgenic *Arabidopsis* lines were inoculated 2 weeks after sowing with a $5\times10^4$ conidiospore suspension of *P. parasitica* isolate NOCO. Flats were covered with a humidity dome and moved to the growth chamber maintained at 18° C., 16 hours light, and 100% humidity. Plants were scored for infection 7 days after inoculation with a disease rating system adapted from Cao et al., "Generation of Broad-Spectrum Disease Resistance by Overexpression of an Essential Regulatory Gene in Systemic Acquired Resistance," *Proc. Natl. Acad. Sci. USA* 95:6531–6536 (1998), which is hereby incorporated by reference. A rating of 1, 0 conidiophores present; 2, 0–5 conidiophores present; 3, 6–20 conidiophores on a few leaves; 4, 6–20 conidiophores on all leaves; 5, 20 or more conidiophores present on all leaves. Inoculated leaves were stained with lactophenol-trypan blue (Keogh et al., "Comparison of Histological and Physiological Responses to Phakopsora Pachyrhizi in Resistant and Susceptible Soybean," *Trans. Br. Mycol. Soc.* 74:329–333 (1980), which is hereby incorporated by reference) to observe the extent of fungal colonization under the microscope.

Plants were selected that lacked segregation of antibiotic resistance in the T3 generation. Lines containing the gst1:hrpN construct ("GN lines") lines were tested for resistance to *P. parasitica* isolate NOCO in an initial screen.

Figure 3A:
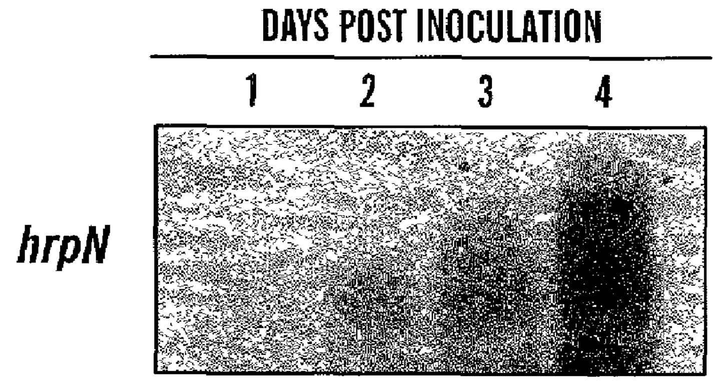
FIGS. 3A and 3B show an analysis of hrpN gene expression in *Arabidopsis* transgenic line GSSN8–4, containing the construct shown in FIG. 1, after inoculation with *P. parasitica* NOCO. At one day intervals leaves were collected for isolation of total RNA.
Figure 3B:
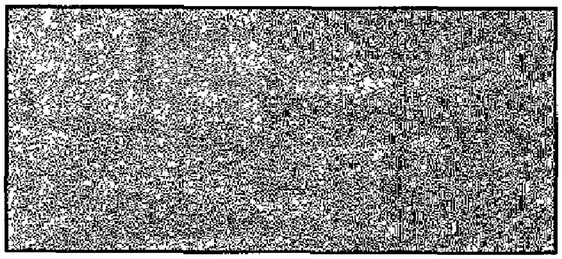

Thirty lines containing the gst1:signal sequence:hrpN construct ("GSSN lines") were tested for resistance to *P. parasitica* isolate NOCO in an initial screen. All but one of the lines was free of any signs of the oomycete ten days after inoculation. Ten GSSN lines were chosen for further study and inoculated by spraying with a conidiospore suspension ($5\times10^4$ spores/ml) of *P. parasitica* NOCO. Northern analysis revealed that expression of hrpN was induced by *P. parasitica* 2 days after inoculation with strong induction at 4 days (FIG. 3A). A range of expression levels were observed among the ten lines, line GSSN 8–4 was chosen for further study as it displayed the highest level of expression. Production of the harpinEa protein in inoculated plants was confirmed by immuno-blot analysis.

RNA was isolated from inoculated plants over a 4 day interval to analyze hrpN gene expression. RNA was isolated from 1 g of plant tissue as described by Carpenter et al., "Preparation of RNA, in *Arabidopsis* Protocols," (Martinez-Zapater, J M. and Salinas, J., eds.), Humana Press, Totowata, N.J., pp. 85–89 (1998). Twenty micro-gram samples were separated by formaldehyde-agarose gel electrophoresis and blotted onto Hybond N+ membranes (Amersham Pharmacia Biotech, Little Chalfont, Buckinghamshire, UK). Hybridizations and washing were performed according to Church et al., "Genomic Sequencing," *Proc. Natl. Acad. Sci. USA* 81:1991–1995 (1984), which is hereby incorporated by reference, using $P^{32}$ labeled hrpN DNA as a probe.

Figure 4A:
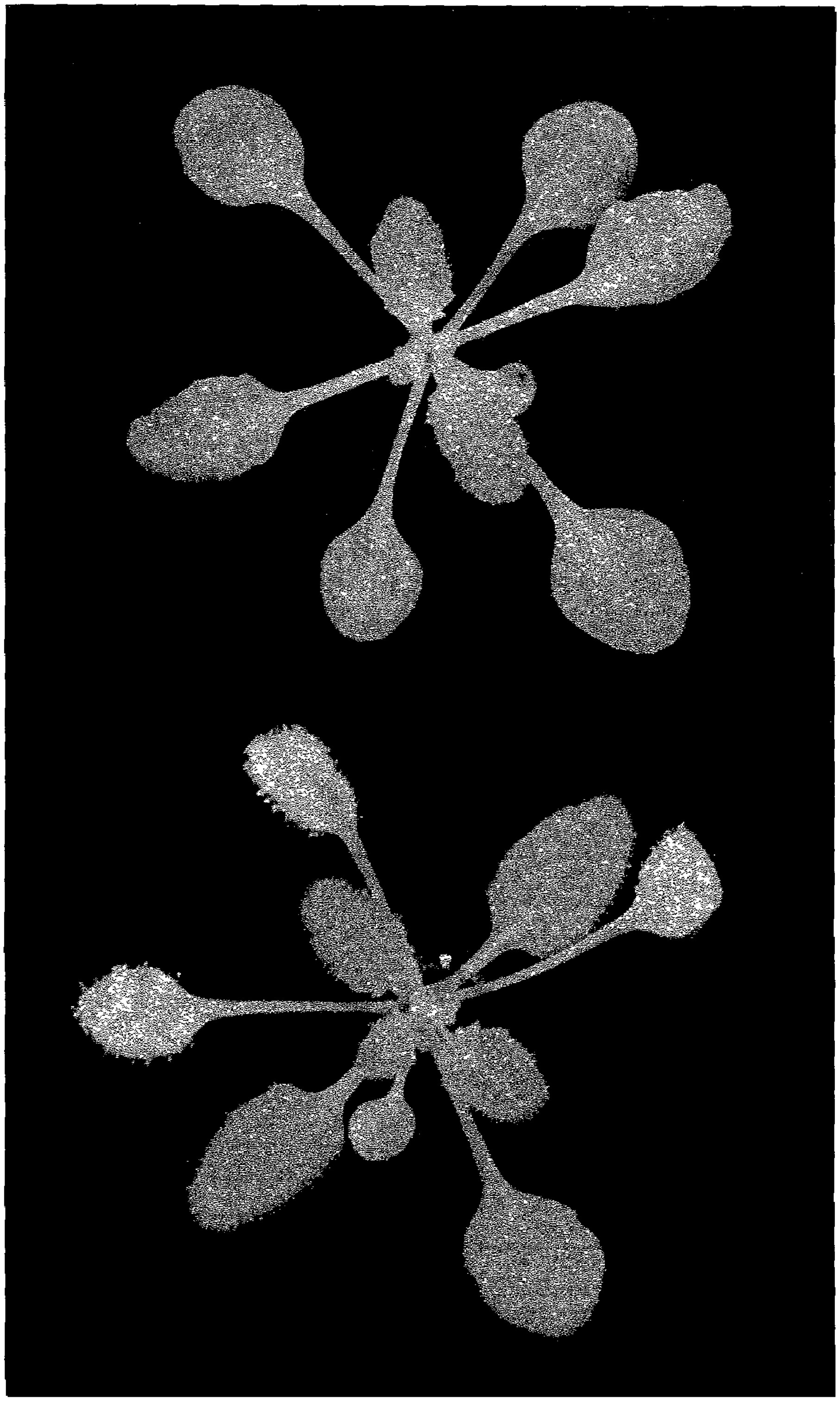
FIGS. 4A and 4B are images demonstrating *Arabidopsis* GSSN 8–4 are resistant to *P. parasitica*.
Figure 4B:

The *Arabidopsis* lines GSSN 8–4 (test), Col-0 WT (wild type, control), and Col-0 EV (empty vector, control) were inoculated by drop inoculation with a conidiospore suspension ($5\times10^4$ spores/ml) of *P. parasitica*. Plants were maintained in a growth chamber (16 hours of light, 18° C., 100% humidity) and were scored for infection ten days post inoculation. Nearly all (29 out of 30) 8–4 plants were free of any signs of *P. parasitica* (FIG. 4A). Trypan blue staining showed that growth of the oomycete was strongly inhibited in GSSN 8–4 plants. Extensive hyphal growth was evident in Col-0 WT and Col-0 EV plants (FIG. 4B).

Figure 5:
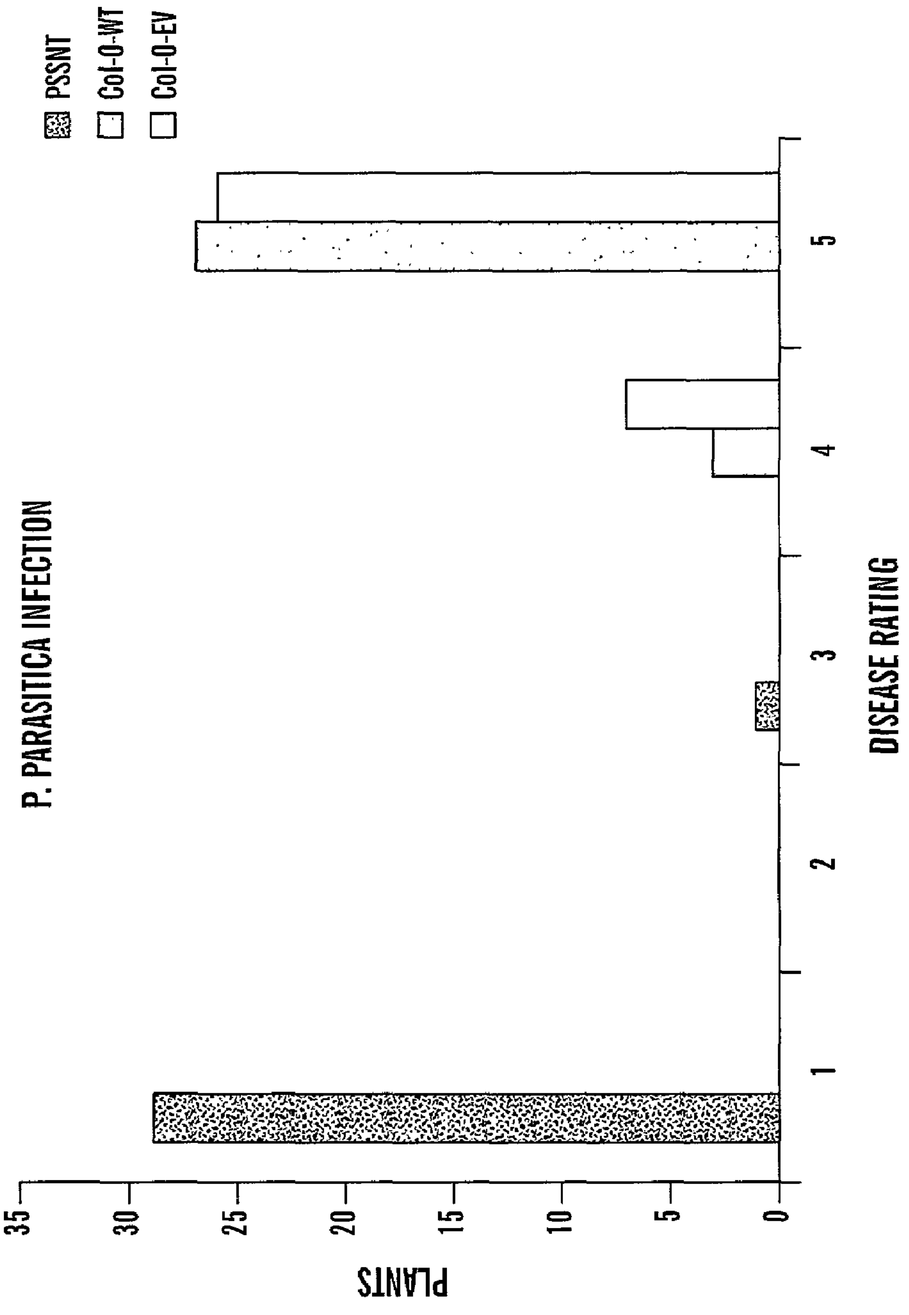
FIG. 5 is a graph depicting the severity of *P. parasitica* infection in WT (control), EV (control), and hrpN transgenic plants (test). Two week old plants were drop inoculated with conidiospores of *P. parasitica* (2 ml drops; $5\times10^4$ spores/ml). Ten days after inoculation, 30 plants of each genotype were rated for disease severity. Ratings were adapted from Cao et al. ("Generation of Broad-Spectrum Disease Resistance by Overexpression of an Essential Regulatory Gene in Systemic Acquired Resistance," *Proc. Natl. Acad. Sci. USA* 95:6531–6536 (1998), which is hereby incorporated by reference) as follows: 1, no conidiophores present on plant; 2, 0–5 conidiophores per infected plant; 3, 6–20 conidiophores present on a few infected leaves; 4, 6–20 conidiophores present on most infected leaves; 5, more than 20 conidiophores on all infected leaves.

Plants were rated for disease severity based on the number of conidiophores per leaf. Nearly all GSSN 8–4 plants received a disease rating of 1 with only one being scored 3. The majority of the Col-0 WT and Col-0 EV plants were rated 5, the remainder were rated 4 (FIG. 5).

This example demonstrates that pathogen inducible expression of the harpinEa hypersensitive response elicitor of *Erwinia amylovora* in transgenic plants is a potentially useful strategy for engineering plants for disease resistance. Challenge with *Peronospora* parasitica resulted in accumulation of hrpN mRNA, production of harpinEa protein, and resistance to *P. parasitica*. Upon challenge by *P. parasitica*, it is believed that the transgenic plants most likely mount a hypersensitive response at the site of inoculation, conferring resistance. Subsequently the plants may develop systemic resistance.

For the purposes of the present invention, the gst1 promoter was most applicable to the *Arabidopsis/P. parasitica* pathosystem since it is well documented that transcription from gst1 is activated by other oomycete pathogens (Martini et al., "Promoter Sequences of a Potato Pathogenesis-related Gene Mediate Transcriptional Activation Selectively upon Fungal Infection," *Mol. Gen. Genet.* 236: (2–3) 179–86 (1993), which is hereby incorporated by reference). Additionally, it has been reported that gst1 activation is stimulated by ascomycete, viral, and nematode infection and mycorrhization (Strittmatter et al., "Infections with Various Types of Organisms Stimulate Transcription From a Short Promoter Fragment of the Potato gst1 Gene," *Mol. Plant-Microbe Interact.* 9:68–73 (1996), which is hereby incorporated by reference). Therefore, it is possible that both gst1:hrpN and gst1:signal sequence:hrpN constructs may also confer resistance against ascomycete, virus, and nematode infection, as well as mycorrhization.

Although the invention has been described in detail for the purpose of illustration, it is understood that such detail is solely for that purpose, and variations can be made therein by those skilled in the art without departing from the spirit and scope of the invention which is defined by the following claims.

All of the references designated as being incorporated herein by reference are intended to be incorporated in their entirety unless specific portions thereof have been identified with particularity.

What is claimed is:

1. A chimeric gene comprising:

a first DNA molecule encoding a hypersensitive response elicitor protein or polypeptide from a bacterial plant pathogen, wherein the encoded hypersensitive response elicitor comprises the amino acid sequence according to SEQ ID NO:1, SEQ ID NO:3, SEQ ID NO:5, or SEQ ID NO:7;

a promoter operably linked 5' to the first DNA molecule to induce transcription of the first DNA molecule in response to activation of the promoter by an oomycete, the promoter comprising nt 295–567 of SEQ ID NO: 9;

a 3' regulatory region operably linked to the first DNA molecule; and a second DNA molecule encoding a secretion signal polypeptide, the second DNA molecule being operably linked between the promoter and the first DNA molecule.

2. The chimeric gene according to claim 1, wherein the second DNA molecule encodes a secretion signal polypeptide comprising the amino acid sequence of SEQ ID NO: 11, SEQ ID NO: 13, SEQ ID NO: 15, or SEQ ID NO: 17.

3. The chimeric gene according to claim 2, wherein the second DNA molecule comprises the nucleotide sequence of nt 8–110 from SEQ ID NO: 10, SEQ ID NO: 12, SEQ ID NO: 14, or SEQ ID NO: 16.

4. The chimeric gene according to claim 1, wherein the first DNA molecule encodes a hypersensitive response elicitor protein or polypeptide comprising the amino acid sequence of SEQ ID NO: 3.

5. The chimeric gene according to claim 4, wherein the first DNA molecule comprises the nucleotide sequence of SEQ ID NO: 4.

6. The chimeric gene according to claim 1, wherein the first DNA molecule encodes a hypersensitive response elicitor protein or polypeptide comprising the amino acid sequence of SEQ ID NO: 1.

7. The chimeric gene according to claim 6, wherein the first DNA molecule comprises the nucleotide sequence of SEQ ID NO: 2.

8. The chimeric gene according to claim 1, wherein the first DNA molecule encodes a hypersensitive response elicitor protein or polypeptide comprising the amino acid sequence of SEQ ID NO: 5.

9. The chimeric gene according to claim 8, wherein the first DNA molecule comprises the nucleotide sequence of SEQ ID NO: 6.

10. The chimeric gene according to claim 1, wherein the first DNA molecule encodes a hypersensitive response elicitor protein or polypeptide comprising the amino acid sequence of SEQ ID NO: 7.

11. The chimeric gene according to claim 10, wherein the first DNA molecule comprises the nucleotide sequence of SEQ ID NO:8.

12. An expression system comprising a vector into which is inserted the chimeric gene according to claim 1.

13. A host cell comprising the chimeric gene according to claim 1.

14. The host cell according to claim 13, wherein the host cell is a bacterial cell or a plant cell.

15. The host cell according to claim 14, wherein the bacterial cell is an *Agrobacterium* cell.

16. The host cell according to claim 14, wherein the host cell is a plant cell.

17. A transgenic plant resistant to disease resulting from oomycete infection, the transgenic plant comprising:

the chimeric gene according to claim 1, wherein the promoter induces transcription of the first DNA molecule in response to infection of the plant by an oomycete.

18. The transgenic plant according to claim 17, wherein the second DNA molecule encodes a secretion signal polypeptide comprising the amino acid sequence of SEQ ID NO: 11, SEQ ID NO: 13, SEQ ID NO: 15, or SEQ ID NO: 17.

19. The transgenic plant according to claim 18, wherein the second DNA molecule comprises the nucleotide sequence of nt 8–110 from SEQ ID NO: 10, SEQ ID NO: 12, SEQ ID NO: 14, or SEQ ID NO: 16.

20. The transgenic plant according to claim 17, wherein the transgenic plant is selected from a group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

21. The transgenic plant according to claim 20, wherein the transgenic plant is a grape plant.

22. The transgenic plant according to claim 20, wherein the transgenic plant is a tobacco plant.

23. The transgenic plant according to claim 17, wherein the first DNA molecule encodes a hypersensitive response elicitor protein or polypeptide comprising the amino acid sequence of SEQ ID NO: 3.

24. The transgenic plant according to claim 23, wherein the first DNA molecule comprises the nucleotide sequence of SEQ ID NO: 4.

25. The transgenic plant according to claim 17, wherein the first DNA molecule encodes a hypersensitive response elicitor protein or polypeptide comprising the amino acid sequence of SEQ ID NO: 1.

26. The transgenic plant according to claim 25, wherein the first DNA molecule comprises the nucleotide sequence of SEQ ID NO: 2.

27. The transgenic plant according to claim 17, wherein the first DNA molecule encodes a hypersensitive response elicitor protein or polypeptide comprising the amino acid sequence of SEQ ID NO: 5.

28. The transgenic plant according to claim 27, wherein the first DNA molecule comprises the nucleotide sequence of SEQ ID NO: 6.

29. The transgenic plant according to claim 17, wherein the first DNA molecule encodes a hypersensitive response elicitor protein or polypeptide comprising the amino acid sequence of SEQ ID NO: 7.

30. The transgenic plant according to claim 29, wherein the first DNA molecule comprises the nucleotide sequence of SEQ ID NO: 8.

31. The transgenic plant according to claim 17, wherein the chimeric gene is stably inserted into the genome of the transgenic plant.

32. A method of making a recombinant plant cell comprising:

transforming a plant cell with the chimeric gene according to claim 1 under conditions effective to yield transcription of the first and second DNA molecules in response to oomycete-induced activation of the promoter.

33. A method of making a plant resistant to disease resulting from oomycete infection, the method comprising:

transforming a plant cell with the chimeric gene according to claim 1, whereby the transformed plant cell expresses the first and second DNA molecules in response to oomycete-induced activation of the promoter and regenerating a plant from the transformed plant cell, wherein following expression of the first and second DNA molecules the regenerated plant is rendered resistant to disease resulting from oomycete infection.

34. The method according to claim 33, wherein said transforming comprises inserting the chimeric gene into the genome of the plant cell.

35. The method according to claim 33, wherein said transforming is *Agrobacterium* mediated.

36. The method according to claim 33, wherein said transforming comprises:

propelling particles at the plant cell under conditions effective for the particles to penetrate into the cell interior, whereby penetrating particles introduce an expression vector comprising the chimeric gene into the plant cell interior.

37. The method according to claim 33, wherein the transgenic plant is selected from the group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

38. The method according to claim 37, wherein the transgenic plant is a grape plant.

39. The method according to claim 37, wherein the transgenic plant is a tobacco plant.

40. A transgenic plant seed obtained from the transgenic plant according to claim 17.

41. A transgenic plant scion or rootstock cultivar obtained from the transgenic plant according to claim 17.

* * * * *

SEQUENCE LISTING

```
<160> NUMBER OF SEQ ID NOS: 26

<210> SEQ ID NO 1
<211> LENGTH: 338
<212> TYPE: PRT
<213> ORGANISM: Erwinia chrysanthemi

<400> SEQUENCE: 1

Met Gln Ile Thr Ile Lys Ala His Ile Gly Gly Asp Leu Gly Val Ser
  1               5                  10                  15

Gly Leu Gly Ala Gln Gly Leu Lys Gly Leu Asn Ser Ala Ala Ser Ser
             20                  25                  30

Leu Gly Ser Ser Val Asp Lys Leu Ser Ser Thr Ile Asp Lys Leu Thr
         35                  40                  45

Ser Ala Leu Thr Ser Met Met Phe Gly Gly Ala Leu Ala Gln Gly Leu
     50                  55                  60

Gly Ala Ser Ser Lys Gly Leu Gly Met Ser Asn Gln Leu Gly Gln Ser
 65                  70                  75                  80
```

-continued

```
Phe Gly Asn Gly Ala Gln Gly Ala Ser Asn Leu Leu Ser Val Pro Lys
                 85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285

Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

<210> SEQ ID NO 2
<211> LENGTH: 2141
<212> TYPE: DNA
<213> ORGANISM: Erwinia chrysanthemi

<400> SEQUENCE: 2

```
cgattttacc cgggtgaacg tgctatgacc gacagcatca cggtattcga caccgttacg      60

gcgtttatgg ccgcgatgaa ccggcatcag gcggcgcgct ggtcgccgca atccggcgtc     120

gatctggtat ttcagtttgg ggacaccggg cgtgaactca tgatgcagat tcagccgggg     180

cagcaatatc ccggcatgtt gcgcacgctg ctcgctcgtc gttatcagca ggcggcagag     240

tgcgatggct gccatctgtg cctgaacggc agcgatgtat tgatcctctg gtggccgctg     300

ccgtcggatc ccggcagtta tccgcaggtg atcgaacgtt tgtttgaact ggcgggaatg     360

acgttgccgt cgctatccat agcaccgacg gcgcgtccgc agacagggaa cggacgcgcc     420

cgatcattaa gataaaggcg gcttttttta ttgcaaaacg gtaacggtga ggaaccgttt     480

caccgtcggc gtcactcagt aacaagtatc catcatgatg cctacatcgg gatcggcgtg     540

ggcatccgtt gcagatactt ttgcgaacac ctgacatgaa tgaggaaacg aaattatgca     600

aattacgatc aaagcgcaca tcggcggtga tttgggcgtc tccggtctgg ggctgggtgc     660
```

-continued

```
tcagggactg aaaggactga attccgcggc ttcatcgctg ggttccagcg tggataaact    720
gagcagcacc atcgataagt tgacctccgc gctgacttcg atgatgtttg gcggcgcgct    780
ggcgcagggg ctgggcgcca gctcgaaggg gctggggatg agcaatcaac tgggccagtc    840
tttcggcaat ggcgcgcagg gtgcgagcaa cctgctatcc gtaccgaaat ccggcggcga    900
tgcgttgtca aaaatgtttg ataaagcgct ggacgatctg ctgggtcatg acaccgtgac    960
caagctgact aaccagagca accaactggc taattcaatg ctgaacgcca gccagatgac   1020
ccagggtaat atgaatgcgt tcggcagcgg tgtgaacaac gcactgtcgt ccattctcgg   1080
caacggtctc ggccagtcga tgagtggctt ctctcagcct tctctggggg caggcggctt   1140
gcagggcctg agcggcgcgg gtgcattcaa ccagttgggt aatgccatcg gcatgggcgt   1200
ggggcagaat gctgcgctga gtgcgttgag taacgtcagc acccacgtag acggtaacaa   1260
ccgccacttt gtagataaag aagatcgcgg catggcgaaa gagatcggcc agtttatgga   1320
tcagtatccg gaaatattcg gtaaaccgga ataccagaaa gatggctgga gttcgccgaa   1380
gacggacgac aaatcctggg ctaaagcgct gagtaaaccg gatgatgacg gtatgaccgg   1440
cgccagcatg gacaaattcc gtcaggcgat gggtatgatc aaaagcgcgg tggcgggtga   1500
taccggcaat accaacctga acctgcgtgg cgcgggcggt gcatcgctgg gtatcgatgc   1560
ggctgtcgtc ggcgataaaa tagccaacat gtcgctgggt aagctggcca acgcctgata   1620
atctgtgctg gcctgataaa gcggaaacga aaaaagagac ggggaagcct gtctcttttc   1680
ttattatgcg gtttatgcgg ttacctggac cggttaatca tcgtcatcga tctggtacaa   1740
acgcacattt tcccgttcat tcgcgtcgtt acgcgccaca atcgcgatgg catcttcctc   1800
gtcgctcaga ttgcgcggct gatggggaac gccgggtgga atatagagaa actcgccggc   1860
cagatggaga cacgtctgcg ataaatctgt gccgtaacgt gtttctatcc gcccctttag   1920
cagatagatt gcggtttcgt aatcaacatg gtaatgcggt tccgcctgtg cgccggccgg   1980
gatcaccaca atattcatag aaagctgtct tgcacctacc gtatcgcggg agataccgac   2040
aaaatagggc agtttttgcg tggtatccgt ggggtgttcc ggcctgacaa tcttgagttg   2100
gttcgtcatc atctttctcc atctgggcga cctgatcggt t                       2141
```

<210> SEQ ID NO 3
<211> LENGTH: 403
<212> TYPE: PRT
<213> ORGANISM: Erwinia amylovora

<400> SEQUENCE: 3

```
Met Ser Leu Asn Thr Ser Gly Leu Gly Ala Ser Thr Met Gln Ile Ser
  1               5                  10                  15

Ile Gly Gly Ala Gly Gly Asn Asn Gly Leu Leu Gly Thr Ser Arg Gln
             20                  25                  30

Asn Ala Gly Leu Gly Gly Asn Ser Ala Leu Gly Leu Gly Gly Gly Asn
         35                  40                  45

Gln Asn Asp Thr Val Asn Gln Leu Ala Gly Leu Leu Thr Gly Met Met
     50                  55                  60

Met Met Met Ser Met Met Gly Gly Gly Gly Leu Met Gly Gly Gly Leu
 65                  70                  75                  80

Gly Gly Gly Leu Gly Asn Gly Leu Gly Gly Ser Gly Gly Leu Gly Glu
                 85                  90                  95

Gly Leu Ser Asn Ala Leu Asn Asp Met Leu Gly Gly Ser Leu Asn Thr
            100                 105                 110
```

-continued

```
Leu Gly Ser Lys Gly Gly Asn Asn Thr Thr Ser Thr Thr Asn Ser Pro
        115                 120                 125

Leu Asp Gln Ala Leu Gly Ile Asn Ser Thr Ser Gln Asn Asp Asp Ser
    130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
        195                 200                 205

Leu Met Gly Asn Gly Leu Ser Gln Leu Leu Gly Asn Gly Gly Leu Gly
    210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
    290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380

Ala Met Met Ala Gly Asp Ala Ile Asn Asn Met Ala Leu Gly Lys Leu
385                 390                 395                 400

Gly Ala Ala


<210> SEQ ID NO 4
<211> LENGTH: 1288
<212> TYPE: DNA
<213> ORGANISM: Erwinia amylovora

<400> SEQUENCE: 4

aagcttcggc atggcacgtt tgaccgttgg gtcggcaggg tacgtttgaa ttattcataa      60

gaggaatacg ttatgagtct gaatacaagt gggctgggag cgtcaacgat gcaaatttct     120

atcggcggtg cgggcggaaa taacgggttg ctgggtacca gtcgccagaa tgctgggttg     180

ggtggcaatt ctgcactggg gctgggcggc ggtaatcaaa atgataccgt caatcagctg     240

gctggcttac tcaccggcat gatgatgatg atgagcatga tgggcggtgg tgggctgatg     300

ggcggtggct taggcggtgg cttaggtaat ggcttgggtg gctcaggtgg cctgggcgaa     360

ggactgtcga acgcgctgaa cgatatgtta ggcggttcgc tgaacacgct gggctcgaaa     420

ggcggcaaca ataccacttc aacaacaaat tccccgctgg accaggcgct gggtattaac     480
```

-continued

```
tcaacgtccc aaaacgacga ttccacctcc ggcacagatt ccacctcaga ctccagcgac    540

ccgatgcagc agctgctgaa gatgttcagc gagataatgc aaagcctgtt tggtgatggg    600

caagatggca cccagggcag ttcctctggg ggcaagcagc cgaccgaagg cgagcagaac    660

gcctataaaa aaggagtcac tgatgcgctg tcgggcctga tgggtaatgg tctgagccag    720

ctccttggca acgggggact gggaggtggt cagggcggta atgctggcac gggtcttgac    780

ggttcgtcgc tgggcggcaa agggctgcaa aacctgagcg ggccggtgga ctaccagcag    840

ttaggtaacg ccgtgggtac cggtatcggt atgaaagcgg gcattcaggc gctgaatgat    900

atcggtacgc acaggcacag ttcaacccgt tctttcgtca ataaaggcga tcgggcgatg    960

gcgaaggaaa tcggtcagtt catggaccag tatcctgagg tgtttggcaa gccgcagtac   1020

cagaaaggcc cgggtcagga ggtgaaaacc gatgacaaat catgggcaaa agcactgagc   1080

aagccagatg acgacggaat gacaccagcc agtatggagc agttcaacaa agccaagggc   1140

atgatcaaaa ggcccatggc gggtgatacc ggcaacggca acctgcaggc acgcggtgcc   1200

ggtggttctt cgctgggtat tgatgccatg atggccggtg atgccattaa caatatggca   1260

cttggcaagc tgggcgcggc ttaagctt                                      1288
```

<210> SEQ ID NO 5
<211> LENGTH: 341
<212> TYPE: PRT
<213> ORGANISM: Pseudomonas syringae

<400> SEQUENCE: 5

```
Met Gln Ser Leu Ser Leu Asn Ser Ser Ser Leu Gln Thr Pro Ala Met
  1               5                  10                  15

Ala Leu Val Leu Val Arg Pro Glu Ala Glu Thr Thr Gly Ser Thr Ser
             20                  25                  30

Ser Lys Ala Leu Gln Glu Val Val Val Lys Leu Ala Glu Glu Leu Met
         35                  40                  45

Arg Asn Gly Gln Leu Asp Asp Ser Ser Pro Leu Gly Lys Leu Leu Ala
     50                  55                  60

Lys Ser Met Ala Ala Asp Gly Lys Ala Gly Gly Gly Ile Glu Asp Val
 65                  70                  75                  80

Ile Ala Ala Leu Asp Lys Leu Ile His Glu Lys Leu Gly Asp Asn Phe
                 85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
                165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205

Thr Gly Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
```

-continued

```
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
        275                 280                 285

Asp Leu Asp Gln Leu Leu Gly Gly Leu Leu Leu Lys Gly Leu Glu Ala
    290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
            340


<210> SEQ ID NO 6
<211> LENGTH: 1026
<212> TYPE: DNA
<213> ORGANISM: Pseudomonas syringae

<400> SEQUENCE: 6

atgcagagtc tcagtcttaa cagcagctcg ctgcaaaccc cggcaatggc ccttgtcctg     60

gtacgtcctg aagccgagac gactggcagt acgtcgagca aggcgcttca ggaagttgtc    120

gtgaagctgg ccgaggaact gatgcgcaat ggtcaactcg acgacagctc gccattggga    180

aaactgttgg ccaagtcgat ggccgcagat ggcaaggcgg gcggcggtat tgaggatgtc    240

atcgctgcgc tggacaagct gatccatgaa aagctcggtg acaacttcgg cgcgtctgcg    300

gacagcgcct cgggtaccgg acagcaggac ctgatgactc aggtgctcaa tggcctggcc    360

aagtcgatgc tcgatgatct tctgaccaag caggatggcg ggacaagctt ctccgaagac    420

gatatgccga tgctgaacaa gatcgcgcag ttcatggatg acaatcccgc acagtttccc    480

aagccggact cgggctcctg ggtgaacgaa ctcaaggaag acaacttcct tgatggcgac    540

gaaacggctg cgttccgttc ggcactcgac atcattggcc agcaactggg taatcagcag    600

agtgacgctg gcagtctggc agggacgggt ggaggtctgg gcactccgag cagtttttcc    660

aacaactcgt ccgtgatggg tgatccgctg atcgacgcca ataccggtcc cggtgacagc    720

ggcaataccc gtggtgaagc ggggcaactg atcggcgagc ttatcgaccg tggcctgcaa    780

tcggtattgg ccggtggtgg actgggcaca cccgtaaaca ccccgcagac cggtacgtcg    840

gcgaatggcg gacagtccgc tcaggatctt gatcagttgc tgggcggctt gctgctcaag    900

ggcctggagg caacgctcaa ggatgccggg caaacaggca ccgacgtgca gtcgagcgct    960

gcgcaaatcg ccaccttgct ggtcagtacg ctgctgcaag gcacccgcaa tcaggctgca   1020

gcctga                                                              1026


<210> SEQ ID NO 7
<211> LENGTH: 344
<212> TYPE: PRT
<213> ORGANISM: Pseudomonas solanacearum

<400> SEQUENCE: 7

Met Ser Val Gly Asn Ile Gln Ser Pro Ser Asn Leu Pro Gly Leu Gln
  1               5                  10                  15

Asn Leu Asn Leu Asn Thr Asn Thr Asn Ser Gln Gln Ser Gly Gln Ser
```

-continued

```
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

<210> SEQ ID NO 8
<211> LENGTH: 1035
<212> TYPE: DNA
<213> ORGANISM: Pseudomonas solanacearum

<400> SEQUENCE: 8

```
atgtcagtcg gaaacatcca gagcccgtcg aacctcccgg gtctgcagaa cctgaacctc      60

aacaccaaca ccaacagcca gcaatcgggc cagtccgtgc aagacctgat caagcaggtc     120

gagaaggaca tcctcaacat catcgcagcc ctcgtgcaga aggccgcaca gtcggcgggc     180

ggcaacaccg gtaacaccgg caacgcgccg gcgaaggacg gcaatgccaa cgcgggcgcc     240

aacgacccga gcaagaacga cccgagcaag agccaggctc cgcagtcggc caacaagacc     300
```

-continued

```
ggcaacgtcg acgacgccaa caaccaggat ccgatgcaag cgctgatgca gctgctggaa    360

gacctggtga agctgctgaa ggcggccctg cacatgcagc agcccggcgg caatgacaag    420

ggcaacggcg tgggcggtgc caacggcgcc aagggtgccg gcggccaggg cggcctggcc    480

gaagcgctgc aggagatcga gcagatcctc gcccagctcg gcggcggcgg tgctggcgcc    540

ggcggcgcgg gtggcggtgt cggcggtgct ggtggcgcgg atggcggctc cggtgcgggt    600

ggcgcaggcg gtgcgaacgg cgccgacggc ggcaatggcg tgaacggcaa ccaggcgaac    660

ggcccgcaga acgcaggcga tgtcaacggt gccaacggcg cggatgacgg cagcgaagac    720

cagggcggcc tcaccggcgt gctgcaaaag ctgatgaaga tcctgaacgc gctggtgcag    780

atgatgcagc aaggcggcct cggcggcggc aaccaggcgc agggcggctc gaagggtgcc    840

ggcaacgcct cgccggcttc cggcgcgaac ccgggcgcga accagcccgg ttcggcggat    900

gatcaatcgt ccggccagaa caatctgcaa tcccagatca tggatgtggt gaaggaggtc    960

gtccagatcc tgcagcagat gctggcggcg cagaacggcg gcagccagca gtccacctcg   1020

acgcagccga tgtaa                                                    1035
```

<210> SEQ ID NO 9
<211> LENGTH: 696
<212> TYPE: DNA
<213> ORGANISM: Solanum tuberosum

<400> SEQUENCE: 9

```
gaattcagga agaattttgt aggttcaact aaattatata tatatatata aaaaaataaa     60

aattattaga cgcttcgact atttacttac tttaaaattt gaattttcgt acgaataaaa    120

ttatttgtca gagaaaagtc ttttagctat tcacatgcta ggaagtttca cttttggtgg    180

atcagtgatt gtatattatt taatatatat caattttctc atcaaactga aaatgaaaga    240

taaaattaat attaaaaact ccattcattt taatttattg tcatgttttg acttgatcca    300

aaatctaaca atttaaaagg ttttaaattt ttgtgctttt ttttaaatta aaaatatgtc    360

aaatatatta aaatatattt tttaaatttt atactaaaaa acatgtcaca tgaatatttg    420

aaattataaa attatcaaaa ataaaaaaag aatatttctt taacaaatta aaattgaaaa    480

tatgataaat aaattaaact attctatcat tgatttttct agccaccaga tttgaccaaa    540

cagtgggtga catgagcaca taagtcatct ttattgtatt ttattactca ctccaaaaat    600

atagggaata tgtttactac ttaatttagt caaatataat tttatattag aataattgaa    660

tagtcaaaca agaaacttta atgcatcctt attttt                              696
```

<210> SEQ ID NO 10
<211> LENGTH: 110
<212> TYPE: DNA
<213> ORGANISM: Nicotiana tabacum

<400> SEQUENCE: 10

```
tctagaccat gggatttttt ctcttttcac aaatgccctc atttttttctt gtgtcgacac     60

ttctcttatt cctaataata tctcactctt ctcatgccca aaactctaga               110
```

<210> SEQ ID NO 11
<211> LENGTH: 34
<212> TYPE: PRT
<213> ORGANISM: Nicotiana tabacum

<400> SEQUENCE: 11

-continued

```
Met Gly Phe Phe Leu Phe Ser Gln Met Pro Ser Phe Phe Leu Val Ser
  1               5                  10                  15

Thr Leu Leu Leu Phe Leu Ile Ile Ser His Ser Ser His Ala Gln Asn
             20                  25                  30

Ser Arg


<210> SEQ ID NO 12
<211> LENGTH: 102
<212> TYPE: DNA
<213> ORGANISM: Nicotiana tabacum

<400> SEQUENCE: 12

atgggatttt ttctcttttc acaaatgccc tcattttttc ttgtctctac acttctctta     60

ttcctaataa tatctcactc ttctcatgcc caaaactctc aa                       102


<210> SEQ ID NO 13
<211> LENGTH: 34
<212> TYPE: PRT
<213> ORGANISM: Nicotiana tabacum

<400> SEQUENCE: 13

Met Gly Phe Phe Leu Phe Ser Gln Met Pro Ser Phe Phe Leu Val Ser
  1               5                  10                  15

Thr Leu Leu Leu Phe Leu Ile Ile Ser His Ser Ser His Ala Gln Asn
             20                  25                  30

Ser Gln


<210> SEQ ID NO 14
<211> LENGTH: 90
<212> TYPE: DNA
<213> ORGANISM: Nicotiana tabacum

<400> SEQUENCE: 14

atgggatttg ttctcttttc acaattgcct tcatttcttc ttgtctctac acttctctta     60

ttcctagtaa tatcccactc ttgccgtgcc                                      90


<210> SEQ ID NO 15
<211> LENGTH: 30
<212> TYPE: PRT
<213> ORGANISM: Nicotiana tabacum

<400> SEQUENCE: 15

Met Gly Phe Val Leu Phe Ser Gln Leu Pro Ser Phe Leu Leu Val Ser
  1               5                  10                  15

Thr Leu Leu Leu Phe Leu Val Ile Ser His Ser Cys Arg Ala
             20                  25                  30


<210> SEQ ID NO 16
<211> LENGTH: 75
<212> TYPE: DNA
<213> ORGANISM: Nicotiana tabacum

<400> SEQUENCE: 16

atggagagag ttaataatta taagttgtgc gtggcattgt tgatcatcag catggtgatg     60

gcaatggcgg cggca                                                      75


<210> SEQ ID NO 17
<211> LENGTH: 25
<212> TYPE: PRT
<213> ORGANISM: Nicotiana tabacum
```

-continued

<400> SEQUENCE: 17

Met Glu Arg Val Asn Asn Tyr Lys Leu Cys Val Ala Leu Leu Ile Ile
1 5 10 15

Ser Met Val Met Ala Met Ala Ala Ala
20 25

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 18
tgacggatcc taggaagttt cacttttggt gg 32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 19
tagcgaattc tatgtgtggt tggtctccct tg 32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 20
tacgtctaga tatgtgtggt tggtctccct tg 32

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 21
atactctaga accatgggtc tgaatacaag tggg 34

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 22
tcatgagctc ttaagccggc ccagcttgcc aagtg 35

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 23

-continued

```
tagaggatcc ctgaatacaa gtgggctggg agcg                          34


<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence:  primer

<400> SEQUENCE: 24

tcatggatcc ttaagccgcg cccagcttgc caagtg                        36


<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence:  primer

<400> SEQUENCE: 25

atactctaga ccatgggatt ttttctcttt tca                           33


<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:  primer

<400> SEQUENCE: 26

aggtctagag ttttgggcat gagaagagtg                               30
```